US012629228B2

(12) United States Patent
VanDerWoude et al.

(10) Patent No.: US 12,629,228 B2
(45) Date of Patent: May 19, 2026

(54) SYSTEMS AND METHODS FOR MANAGING SURGICAL SPONGES

(71) Applicant: Stryker Corporation, Kalamazoo, MI (US)

(72) Inventors: Brian James VanDerWoude, Portage, MI (US); Caroline Weinberg, Portage, MI (US); Fazel Yavari, Portage, MI (US); Kristopher Kendall Biegler, Madison, WI (US); Jonathon Emanuel Koenig, Waukesha, WI (US); Alex Surasky-Ysasi, Madison, WI (US); Tyler Toy, Union City, CA (US); Rachel Wallace, Monona, WI (US); Colin Vincent Beney, Sun Prairie, WI (US); Kenneth Lee Soliva, Madison, WI (US)

(73) Assignee: Stryker Corporation, Portage, MI (US)

( * ) Notice: Subject to any disclaimer, the term of this patent is extended or adjusted under 35 U.S.C. 154(b) by 205 days.

(21) Appl. No.: 18/278,948

(22) PCT Filed: Feb. 24, 2022

(86) PCT No.: PCT/US2022/017664
§ 371 (c)(1),
(2) Date: Aug. 25, 2023

(87) PCT Pub. No.: WO2022/182849
PCT Pub. Date: Sep. 1, 2022

(65) Prior Publication Data
US 2024/0130822 A1    Apr. 25, 2024
US 2024/0225772 A9    Jul. 11, 2024

Related U.S. Application Data

(60) Provisional application No. 63/154,147, filed on Feb. 26, 2021.

(51) Int. Cl.
B32B 43/00      (2006.01)
A61B 50/37      (2016.01)
A61B 90/00      (2016.01)

(52) U.S. Cl.
CPC .............. A61B 50/37 (2016.02); A61B 90/08 (2016.02); *A61B 2050/375* (2016.02);
(Continued)

(58) Field of Classification Search
CPC ............. B32B 43/006; Y10T 156/1168; A61B 50/37
See application file for complete search history.

(56) References Cited

U.S. PATENT DOCUMENTS 3,749,237 A    7/1973   Dorton
4,295,537 A   10/1981   McAvinn et al.
(Continued)

FOREIGN PATENT DOCUMENTS

JP    2014204823 A   10/2014
WO    2017112051 A1   6/2017
(Continued)

OTHER PUBLICATIONS

Hottinger Bruel & Kjaer (HBK), "How Does A Bending Beam Load Cell Work? Webpage", https://www.hbkworld.com/en/knowledge/resource-center/articles/2023/how-does-a-bending-beam-load-cell-work#!ref_www.hbm.com, 2023, 12 pages.
(Continued)

*Primary Examiner* — Philip C Tucker
*Assistant Examiner* — Nickolas R Harm
(74) *Attorney, Agent, or Firm* — Howard & Howard Attorneys PLLC

(57)        ABSTRACT
Systems and methods for managing surgical sponges. A dispenser assembly coupled to a main support includes an internal or first storage location to removably receive a carton of sponge sorters, and an external or second storage
(Continued)

location to removably support a carton of surgical draping. At least one arm may be supported on the housing and movable between an undeployed position and a deployed position. The arm may include weighing means to measure a weight of the surgical sponge being disposed in a sponge sorter supported by the arm. The arm may be a cantilever and abeam load cell may be disposed within a channel of a beam. A processor may determine fluid weight based on measured weight and dry weight correlated with the surgical sponge being counted out as detected with a data reader. The processor may estimate blood loss to be displayed on a display.

17 Claims, 25 Drawing Sheets

(52) U.S. Cl.
CPC ..... *A61B 2090/0805* (2016.02); *B32B 43/006* (2013.01); *Y10T 156/1168* (2015.01)

(56) References Cited

U.S. PATENT DOCUMENTS

| | | | |
|---|---|---|---|
| 5,629,498 | A | 5/1997 | Pollock et al. |
| 5,923,001 | A | 7/1999 | Morris et al. |
| 6,390,311 | B1 | 5/2002 | Belokin |
| 6,607,170 | B1 | 8/2003 | Hoftman |
| 7,180,014 | B2 | 2/2007 | Farber et al. |
| 8,371,448 | B1 | 2/2013 | Reaux |
| 8,544,660 | B2 | 10/2013 | Foley |
| 9,198,727 | B1 | 12/2015 | Samuels et al. |
| 9,530,036 | B2 | 12/2016 | Fleck et al. |
| 10,528,782 | B2 | 1/2020 | Satish et al. |
| 10,641,644 | B2 | 5/2020 | Satish et al. |
| 2009/0314906 | A1 | 12/2009 | Cote |
| 2012/0095422 | A1 | 4/2012 | Morris et al. |
| 2013/0088354 | A1 | 4/2013 | Thomas |
| 2015/0168207 | A1 | 6/2015 | Pollock et al. |
| 2017/0258547 | A1 | 9/2017 | Karasina |
| 2020/0170743 | A1* | 6/2020 | Aljuri .................. A61B 46/10 |
| 2021/0052342 | A1 | 2/2021 | Rosinski |

FOREIGN PATENT DOCUMENTS

| | | | |
|---|---|---|---|
| WO | 2021041795 | A1 | 3/2021 |
| WO | 2021097197 | A1 | 5/2021 |

OTHER PUBLICATIONS

International Search Report for Application No. PCT/US2022/017664 dated Jun. 3, 2022, 3 pages.

English language abstract and machine-assisted English translation for JP 2014-204823 A extracted from espacenet.com database on Aug. 14, 2025, 8 pages.

* cited by examiner

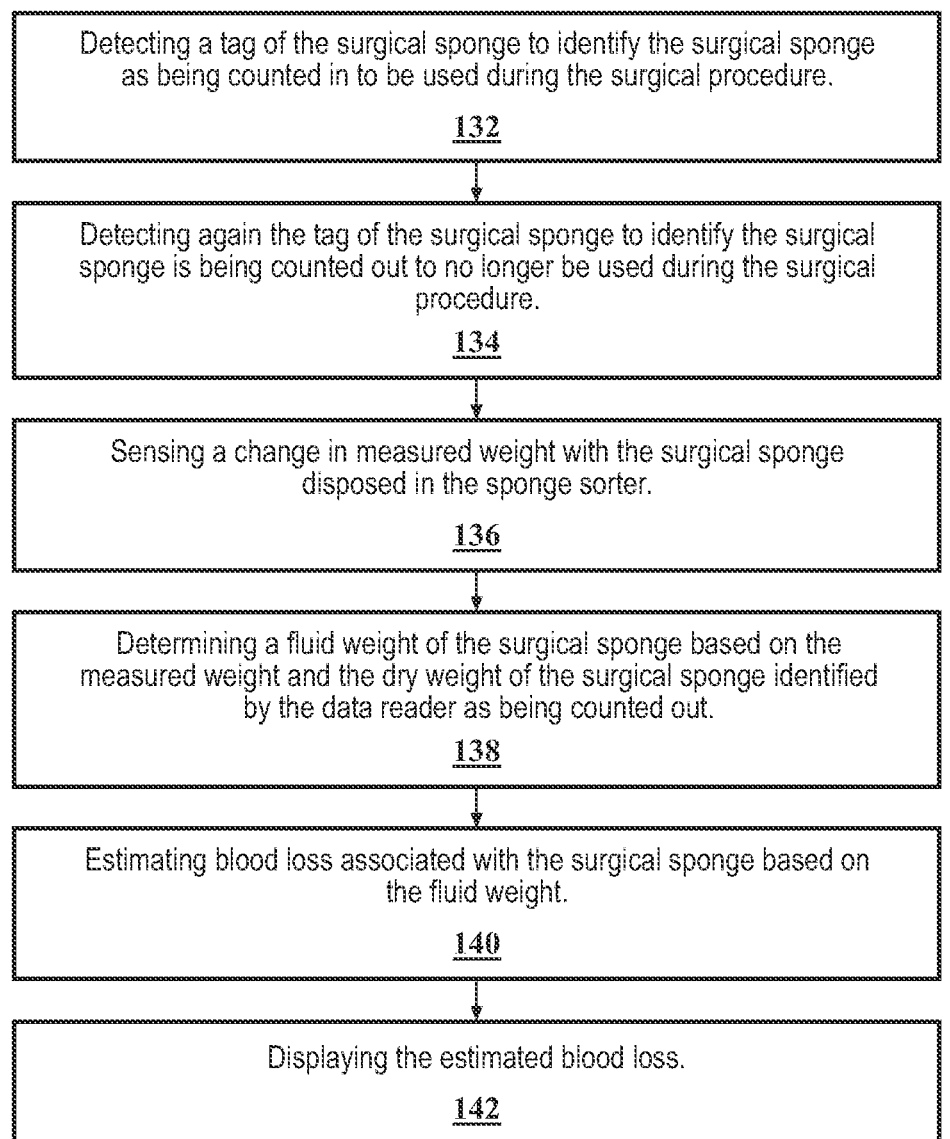

130

Detecting a tag of the surgical sponge to identify the surgical sponge as being counted in to be used during the surgical procedure.

132

Detecting again the tag of the surgical sponge to identify the surgical sponge is being counted out to no longer be used during the surgical procedure.

134

Sensing a change in measured weight with the surgical sponge disposed in the sponge sorter.

136

Determining a fluid weight of the surgical sponge based on the measured weight and the dry weight of the surgical sponge identified by the data reader as being counted out.

138

Estimating blood loss associated with the surgical sponge based on the fluid weight.

140

Displaying the estimated blood loss.

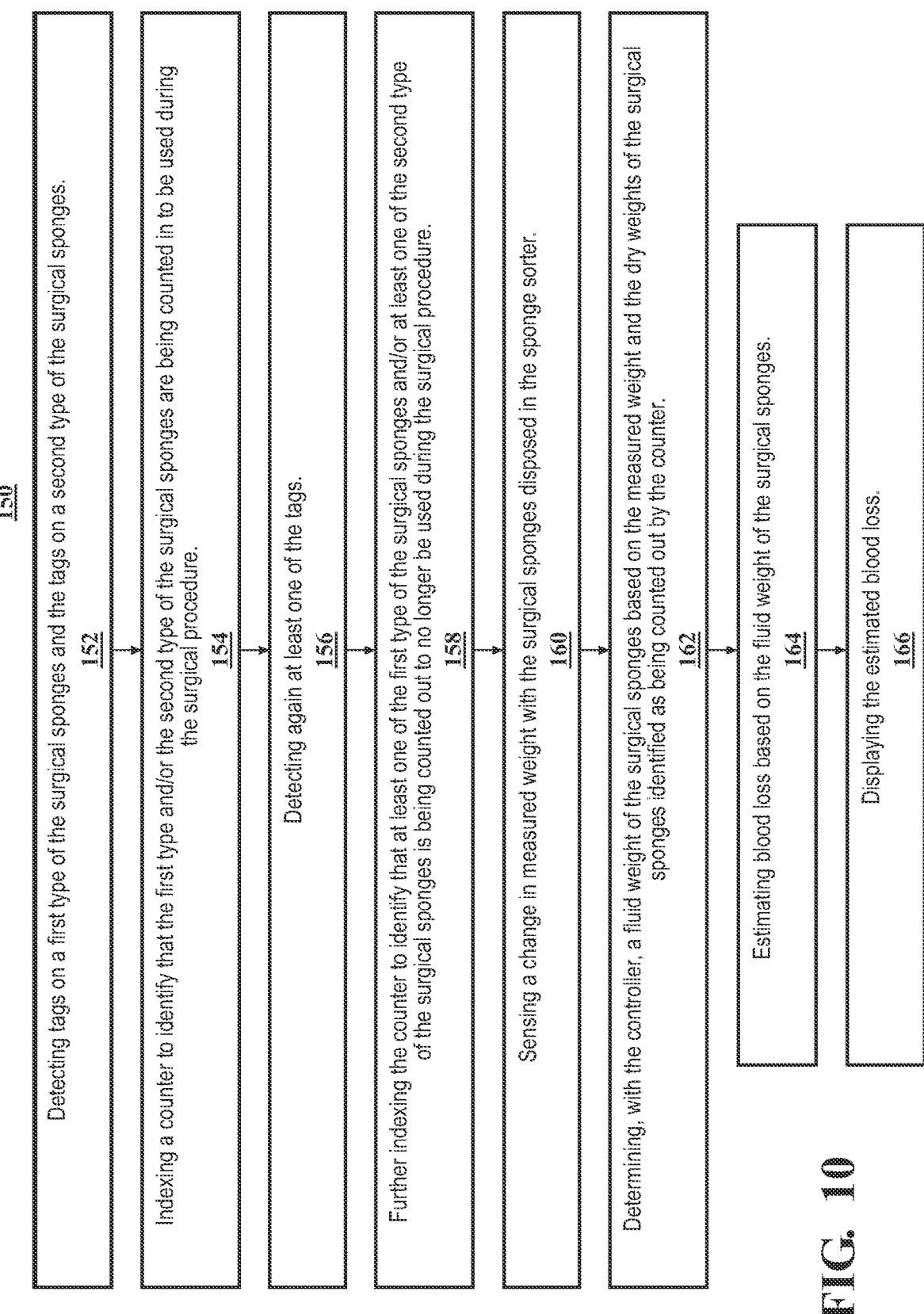

Detecting tags on a first type of the surgical sponges and the tags on a second type of the surgical sponges.
152

Indexing a counter to identify that the first type and/or the second type of the surgical sponges are being counted in to be used during the surgical procedure.
154

Detecting again at least one of the tags.
156

Further indexing the counter to identify that at least one of the first type of the surgical sponges and/or at least one of the second type of the surgical sponges is being counted out to no longer be used during the surgical procedure.
158

Sensing a change in measured weight with the surgical sponges disposed in the sponge sorter.
160

Determining, with the controller, a fluid weight of the surgical sponges based on the measured weight and the dry weights of the surgical sponges identified as being counted out by the counter.
162

Estimating blood loss based on the fluid weight of the surgical sponges.
164

Displaying the estimated blood loss.
166

SYSTEMS AND METHODS FOR MANAGING SURGICAL SPONGES

This is a national entry of International Application No. PCT/US2022/017664, filed Feb. 24, 2022, which claims priority to and all the benefits of U.S. Provisional Patent Application No. 63/154,147, filed Feb. 26, 2021, the entire contents of each being hereby incorporated by reference.

BACKGROUND

Managing surgical sponges is a ubitquitous area of importance in the modern surgical suite, most importantly, ensuring that no surgical sponges (or other objects) are inadvertently retained inside a patient or otherwise misplaced. The surgical sponge is an example of such a surgical article, and therefore health care professionals (HCPs) must follow procedures to account for each and every surgical sponge used during a surgery in view of the obvious issues associated with a surgical article being inadvertently retained inside a patient.

In the past, HCPs have relied upon manual sorting and counting of surgical sponges. Manual sorting and counting of sponges requires handling of and exposure to soiled sponges, and is prone to human error. To facilitate the manual sorting and counting of the surgical sponges, known devices may provide a stand from which a sponge sorter is removably hung. One such stand and sponge sorter is disclosed in U.S. Pat. No. 6,607,170, issued Aug. 19, 2003, hereby incorporated by reference in its entirety, in which a wire basket is positioned atop the stand having conventional hooks to support the sponge sorter having pouches or pockets each for receiving one of the surgical sponges. For any number of reasons it may be indicated to replace the sponge sorter, for example, all of the pockets of the sponge sorter are used yet there are uncounted sponges remaining. Another example includes replacing the sponge sorter between surgical procedures. In such instances, it is inconvenient for the HCP to leave the immediate area to locate the reserves of the unused sponge sorters, or alternatively it is inefficient to consume valuable table space in the immediate area to more conveniently position the unused items at the ready.

More recently, surgical sponge management systems have utilized electronics to assist with counting the surgical sponges. One such system is disclosed in United States Patent Publication No. 2013/0088354, published Apr. 11, 2013, hereby incorporated by reference in its entirety, in which a radiofrequency identification (RFID) reader detects RFID tags on the surgical sponges. The electronics-based devices are typically unable to be sterilized (e.g., autoclaved), and therefore it may be indicated to cover the RFID reader with surgical draping. Between surgical procedures, for example, replacing the surgical draping again inconveniently requires the HCP locate reserves of the unused surgical draping, or alternatively consume the table space.

Moreover, an area of increasing interest and development is estimating or quantifying blood loss. Determining blood loss during surgery may be used to monitor patient health with excessive blood loss indicative of surgical complications. Of particular interest is childbirth, where earlier detection of obstetric hemorrhage may significantly reduce the maternal morbidity rate. It is known to estimate blood loss during surgery by visual evaluation of the surgical sponges and other fluid-absorbing articles (e.g., surgical gowns, bedding, or drapes), which is inherently subjective and therefore prone to human error. It is also known to estimate blood loss during surgery by weighing the surgical sponges on a scale in bulk. In instances where a user interface may provide for selection of the types of surgical sponges being weighed, the fluid weight of the surgical sponges may be calculated based on stored dry weights, which can be converted into an estimated blood loss. While weighing the surgical sponges is more accurate than visual evaluation, it is highly disruptive to the workflow in the surgical suite. In particular, the user must transport the surgical sponges to the scale to be weighed before transporting them to the surgical sponge management system to be checked or counted out, or vice versa.

Therefore, there is a need in the art to provide for an improved surgical sponge management system that overcomes one or more of the aforementioned disadvantages.

SUMMARY

A system for managing surgical sponges, and methods of estimating blood loss with the surgical sponge management system. The system as disclosed herein may be modified to manage fluid-absorbing articles other than surgical sponges, and/or items such as surgical devices and other disposable or reusable instrumentation or objects. The surgical sponge management system includes a stand, an electronics subsystem, and a dispenser assembly. The stand may include a main support coupled to and extending upwardly from a base. The main support may be at least partially hollow to accommodate power and/or data cables. The electronics subsystem includes a module base, a display, and a data reader. The module base may include a processor, memory, communications device, and/or other hardware. The electronics subsystem may be coupled to the main support between the handle and the dispenser assembly. The data reader is configured to detect tags associated with the surgical sponges.

The dispenser assembly is mounted to the main support, and the dispenser assembly may sit atop the stand. The dispenser assembly provides storage and ergonomic dispensing of sponge sorters from a carton of the sponge sorters, and surgical draping from a carton of the surgical draping. A housing of the dispenser assembly may include an upper shell coupled to a lower shell. The lower shell may include lower sidewalls extending upwardly from a lower wall. The lower wall may slope downwardly from the rear to the front. The dispenser assembly includes at least one mounting bracket coupling arms to the housing. The arms may be positioned within recesses defined by flanged walls and the lower sidewalls in an undeployed position. The arms may be pivotably coupled to and extending rearwardly from the mounting brackets to be movable from the undeployed position to a deployed position in which the arms extend outwardly beyond the sidewalls of the housing. Sorter couplers coupled to the arms are configured to support the sponge sorters.

The upper shell includes the front wall, an upper wall, and upper sidewalls that define an internal or first storage location. With the upper sidewalls of the upper shell secured to the lower sidewalls of the lower shell, the first storage location is formed between the front wall, the upper wall, and the sidewalls. The first storage location is sized to receive the carton of the sponge sorters. The housing defines a rear opening in communication with the first storage location, and the front opening in communication with the first storage location. A dispensing opening of the carton is accessible through the front opening. An external or second storage location provides for storage and ergonomic dispensing of the surgical draping. The second storage location may be generally defined by a recess within the upper wall of the upper shell. The upper shell may include a first retention geometry and a second retention geometry that at least partially forms the second storage location. The first retention geometry and the second retention geometry may be frames extending widthwise across the housing and spaced apart from one another to constrain the carton from moving in the forward and rearward directions. The second storage location may be further formed by a third retention geometry and a fourth retention geometry. The third retention geometry and the fourth retention geometry may be frames extending depthwise along the upper sidewalls and spaced apart from one another to constrain the carton from moving in the lateral directions. The third retention geometry or the fourth retention geometry may define a slot to be aligned with a dispenser opening of the carton of the surgical draping.

The arms may include weighing means such as a load cell, and in particular a bending beam load cell. The arm may be cantilevered and supported by the main support. The arm may further include a beam and a loading bar. The beam is coupled to the housing of the dispenser assembly, and the sorter couplers are coupled to the loading bar. The load cell couples the loading bar to the beam. A first portion or end of the load cell may be fixedly secured to the beam, and a second portion or end of the load cell may be fixedly secured to the loading bar. The beam may define a channel, and the load cell may be disposed within the channel. Alternatively, the load cell may be coupled to an underside of the beam. The arm may include a load limit plate fixedly secured to a mounting block. A gap adjustment screw may be threadedly coupled to the load limit plate. The gap adjustment screw may be selectively adjusted to a desired position. A set screw may be provided to fix the gap adjustment screw in the desired position. The weighing means is in communication with the processor. Alternatively, the weighing means may be in wireless communication with a remote processor such that processing steps may be performed remotely. The weighing means is configured to sense a measured weight of the objects supported by the arm.

Exemplary methods of estimating blood loss may include counting in the surgical sponge by causing the tag to be detected by the data reader. The tag includes identifying data from which the processor is configured to determine a type of the surgical sponge. The type of the surgical sponge is associated with a dry weight that is stored in the memory. Based on the data reader detecting the tag, the processor may index a counter of the quantity of surgical sponges to be used during the surgical procedure. The counter may be displayed on the display. The tags of the surgical sponges are again positioned to be detected by data reader to identify the surgical sponge as being counted out to no longer be used during the surgical procedure. The processor may index the counter, and display the counter on the display. The weighing means may automatically detect or sense a change in the measured weight. The processor is configured to determine a fluid weight of the fluid absorbed by the surgical sponge based on the measured weight and the dry weight of the surgical sponge identified by the data reader as being counted out. The dry weight is subtracted from the measured weight to equal the fluid weight for the surgical sponge that was counted out. A status and the fluid weight for each one of the surgical sponges may be logged and stored in memory for later review and input. The processor estimates blood loss associated with the surgical sponge based on the fluid weight. The processor transmits the data to be displayed on the display. Another exemplary method includes more than one type of surgical sponge being used in the surgical procedure.

The method may include taring the weight to compensate for a tare weight of the sponge sorter. The weighing means may sense the tare weight being equal to or below a predetermined magnitude. Additionally or alternatively, the user may provide an input to the display to tare the weighing means with the sponge sorter supported by the arm. The processor determines the fluid weight of the surgical sponge(s) based on a calculated difference between the measured weight, and the dry weight(s) and the tare weight.

The method may include determining whether the change in the measured weight is correlated to the surgical sponge being counted out. If the change in the measured weight is not correlated to the surgical sponge being counted out, an alert may be provided on the display. The processor may identify if no previous or subsequent detection of the tag has occurred. Additionally or alternatively, the processor may compare a measured duration against a maximum duration between the detection of the tag of the surgical sponge and the change in the measured weight. Additionally or alternatively, the processor may compare the change in the measured weight against a preset maximum sponge weight indicative of a blood-saturated sponge. Lastly, the processor may compare the change in the measured weight against a preset minimum sponge weight. If the change in the measured weight is below the preset minimum, the processor may not correlate the change in the measured weight for estimation of blood loss. If the processor correlates the change in the measured weight to the surgical sponge being counted out, the processor may proceed with the steps of determining the fluid weight of the surgical sponge based on the measured weight and the dry weight, estimating the blood loss associated with the surgical sponge based on the fluid weight, and facilitating the display of the estimated blood loss.

A graphical user interface (GUI) may be displayed on the display. The display may be a touchscreen display providing a user interface for user input. The GUI may include various tiles and information. A tile may display a net fluid volume of the fluid collected during the surgical procedure that is not absorbed by the surgical sponges or the other fluid-absorbing articles. A tile may display the quantity and recorded date and time of the counting bags (e.g., the sponge sorters). A tile may display data associated with the compatible surgical sponges, and the counter may be displayed on a list field.

Based on the gross weight sensed by the weighing means and the tare weight of the counting bags, the fluid weight of the compatible surgical sponges is determined and displayed in a tile. The estimated blood loss may be calculated or recalculated, and displayed in a tile. Another tile may be provided for other fluid-absorbing articles that are not compatible surgical sponges. In instances where processor determines that the change in the measured weight is not correlated to the counting out of a compatible surgical sponge, tiles may be altered to be selected by the user to identify the fluid-absorbing article from an article list field. The GUI may provide a summary field with a breakdown of the type and quantity of the fluids that are represented in each of the net fluid volume, the weighed item volume, and the estimated blood loss. The GUI may also provide the option to exclude the surgical sponges determined to have absorbed mostly or only non-blood fluids. The surgical sponge may be detected by the data reader, or an excluded sponge field may be populated to list the surgical sponge(s) selectable to be excluded.

Therefore, according to a first aspect of the present disclosure, the system for managing surgical sponges includes the main support extending from the base, and the dispenser assembly supported on the main support. The dispenser assembly includes the housing including the first storage location that is internal to the housing with the first storage location configured to removably receive the carton of sponge sorters, and the second storage location that is external to the housing with the second storage location configured to removably support the carton of surgical draping. The housing of the dispenser assembly includes the upper wall forming the second storage location. The first retention geometry and the second retention geometry are spaced are apart from one another to define the second storage location. The third retention geometry and the fourth retention geometry are spaced apart from one another to further define the second storage location. The third retention geometry or the fourth retention geometry may define the slot. The upper shell may include the front wall defining the front opening in communication with the first storage location. The lower wall may slope downwardly towards the front wall.

According to a second aspect of the present disclosure, the system for managing surgical sponges includes the main support extending from the base, and the dispenser assembly supported atop the main support. The dispenser assembly includes the first storage location for removably receiving the carton of sponge sorters, and the second storage location for removably receiving the carton of surgical draping. The electronics subsystem is supported on the main support, and includes the module base, the display removably coupled to the module base, and the data reader removably coupled to the module base. The electronics subsystem may be supported on the main support between the base and the dispenser assembly. The system of the second aspect of the present disclosure that includes the electronics subassembly may be provided on the system of the first aspect.

According to a third aspect of the present disclosure, the system for managing surgical sponges includes the main support supported by the base, and an arm supported by the main support. The arm includes the distal end that is unsupported to provide a cantilever. The load cell is coupled to the cantilever for sensing the combined weight of the sponge sorter supported by the arm and the surgical sponges disposed in the sponge sorter. The arm may extend from the dispenser assembly to provide the cantilever. The proximal end of the arm may be pivotably coupled to the dispenser assembly. The arm may include the beam defining the channel, and the load cell may be disposed within or coupled to an underside of the beam. The system of the third aspect of the present disclosure that includes the arm and the load cell may be provided on the system of the first and/or second aspects.

According to a fourth aspect of the present disclosure, the system for managing surgical sponges includes the main support supported by the base, and an arm supported by the main support. The arm includes the beam, the loading bar, and the load cell for sensing the combined weight of the sponge sorter supported by the arm and the surgical sponges disposed in the sponge sorter. The first end or portion of the load cell is fixedly secured to the beam, and the second end or portion of the load cell is fixedly secured to the loading bar. The arm may include at least one sorter coupler coupled to the loading bar and configured to directly support the sponge sorter. The arm may include the load limit plate fixedly secured to the loading bar and fixedly secured near the second end or portion of the load cell, and the gap adjustment screw threadably coupled to the load limit plate. The adjustment set screw may be threadably coupled to the load limit plate and configured to selectively lock the gap adjustment screw in position. The system of the fourth aspect of the present disclosure that includes the arm and the load cell may be provided on the system of the first and/or second aspects.

According to a fifth aspect of the present disclosure, a method of estimating blood loss includes detecting, with the data reader, the tag of the surgical sponge to identify the surgical sponge as being counted in to be used during the surgical procedure. The type of the surgical sponge has the dry weight that is stored in the memory. The tag of the surgical sponge is detected again with the data reader to identify the surgical sponge as being counted out to no longer be used during the surgical procedure. The change in measured weight is sensed with the weighing means with the surgical sponge disposed into or disposed in the sponge sorter. The fluid weight of fluid on the surgical sponge is determined with the processor based on the measured weight and the dry weight of the surgical sponge as identified by the data reader as being counted out. The blood loss associated with the surgical sponge is estimated with the processor based on the fluid weight. The estimated blood loss is displayed on the display. The tare weight the sponge sorter may be sensed by the weighing means. The fluid weight of the surgical sponge may be determined with the processor based on the measured weight, the dry weight, and the tare weight.

According to a sixth aspect of the present disclosure, a method of estimating blood loss includes detecting, with the data reader, the tags on the first type of the surgical sponges and the tags on the second type of the surgical sponges. The first type has the first dry weight that is stored on the memory and the second type has the second dry weight that is stored on the memory. The counter is indexed with the processor to identify the first type and the second type of the surgical sponges as being counted in to be used during the surgical procedure. At least one of the tags is detected again with the data reader. The counter is further indexed with the processor to identify at least one of the first type of the surgical sponges and/or at least one of the second type of the surgical sponges as being counted out to no longer be used during the surgical procedure. The change in measured weight is sensed with the weighing means with the surgical sponges disposed in the sponge sorter. The fluid weight of the surgical sponges is determined with the processor based on the measured weight and the dry weights of the surgical sponges identified as being counted out by the counter. The blood loss is estimated with the processor based on the fluid weight of the surgical sponges. The estimated blood loss is displayed on the display. The display may also display the counter indicating the quantity of each of the first type and the second type of the surgical sponges that have been counted out and/or counted in.

According to a seventh aspect of the present disclosure, a method of estimating blood loss includes detecting, with the data reader, the tag of the surgical sponge to identify the surgical sponge as being counted in to be used during the surgical procedure. The type of the surgical sponge has the dry weight that is stored on the memory. The change in measured weight is sensed with the weighing means. The processor determines whether the change in the measured weight is correlated to the surgical sponge being counted out. An alert is provided on the display if the change in the measured weight is not correlated to the surgical sponge being counted out. The processor may compare, against the maximum duration, the measured duration between the detection of the tag of the surgical sponge and the change in the measured weight. The processor may compare the change in the measured weight against the preset maximum sponge weight indicative of the blood-saturated sponge. The processor may compare the change in the measured weight against the preset minimum sponge weight. A user input may be received in response to the alert that indicates the type of fluid-absorbing article disposed in the sponge sorter. Another user input may be received that identifies a surgical sponge as being saturated with non-blood fluid. A modified measured weight may be determined with the processor based on the weight of the surgical sponge by being subtracted from the measured weight. The blood loss may be estimated with the processor based on the modified measured weight.

BRIEF DESCRIPTION OF THE DRAWINGS

Referring now to the drawings, exemplary illustrations are shown in detail. Although the drawings represent schematic illustrations, the drawings are not necessarily to scale, and certain features may be exaggerated to better illustrate and explain an innovative aspect of an illustrative example. Further, the exemplary illustrations described herein are not intended to be exhaustive or otherwise limiting or restricting to the precise form and configuration shown in the drawings and disclosed in the following detailed description.

FIG. 9 is a method of estimating blood loss with the system.

FIG. 10 is another method of estimating blood loss with the system.

DETAILED DESCRIPTION

Figure 1:
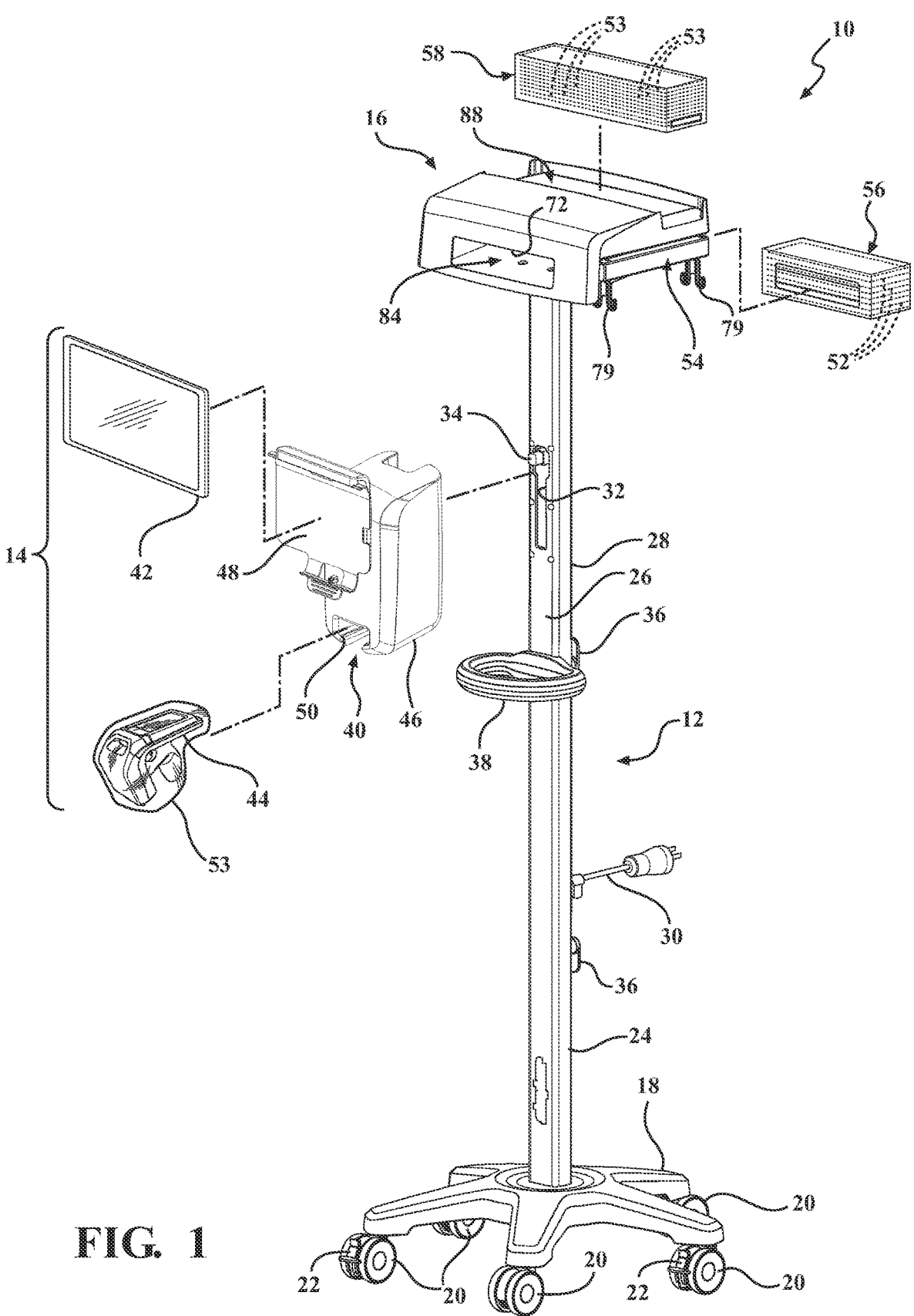
FIG. 1 illustrates a system for managing surgical sponges. A module base, a data reader, and a display are shown decoupled from a mobile stand. A carton of sponge sorters and a carton of surgical draping are shown as being spaced from their respective storage locations on a dispenser assembly. The surgical draping is covering the data reader.
Figure 2:
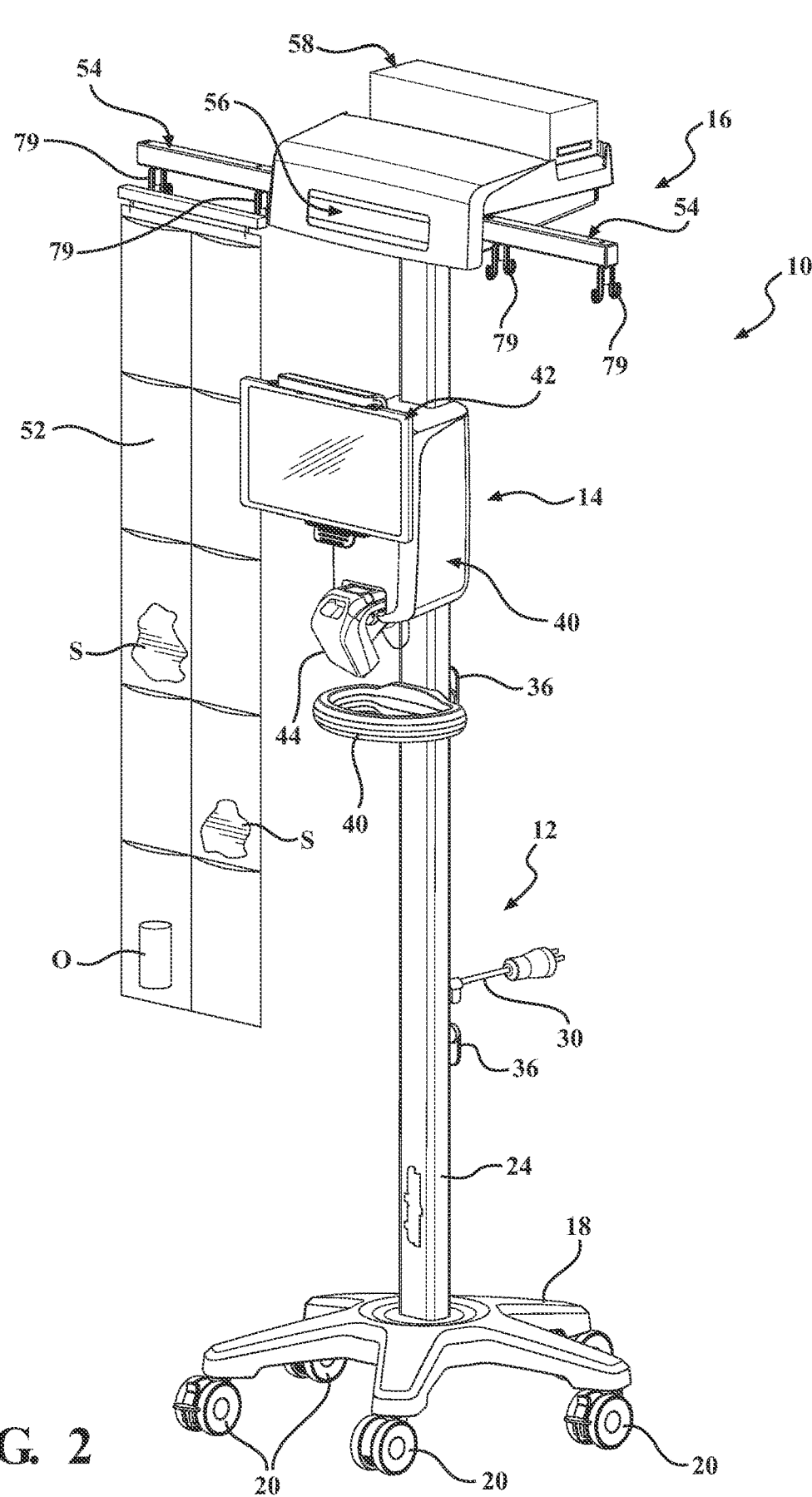
FIG. 2 illustrates the system in a configuration in which at least one arm is deployed outwardly from a housing of the dispenser assembly, and a sponge sorter is suspended from the arm.

The present disclosure relates to a system for managing surgical sponges during a surgical procedure, and thereby prevent retention of the surgical sponges within the patient. The system may further facilitate estimating blood loss associated with the surgical articles in a seamless workflow to be described. Referring to FIGS. 1 and 2, a surgical sponge management system 10 includes a stand 12, an electronics subsystem 14, and a dispenser assembly 16. The stand 12 includes a base 18 that is wheeled so as to maneuver the surgical sponge management system 10 within a medical facility. The wheels may be casters 20 coupled to the base 18 with at least one of the casters 20 including a brake 22 configured to selectively lock the caster(s) 20. The stand 12 may include a main support 24 coupled to and extending upwardly from the base 18. The main support 24 may be a cylindrical pole, or may be square or rectangular in axial section so as to facilitate improved mounting of the electronics subsystem 14. In particular, the main support 24 may include a relatively wider opposing pair of sides 26, 28 with one of the opposing pair of sides 26 being a front of the surgical sponge management system 10 and another one of the opposing pair of sides 28 being a rear of the surgical sponge management system 10. The main support 24 may be at least partially hollow to accommodate power and/or data cables 30 extending therethrough. The illustrated implementation shows the front side 26 defining an opening 32 with a power connector 34 positioned within or adjacent the opening 32. The power cable 30 extends through the main support 24 and exits through another opening (not shown) in the rear side 28 of the main support 24. With the electronics subsystem 14 coupled to the main support 24 as shown in FIG. 2, the power cable 30 may be coupled to an external power source to power the surgical sponge management system 10. It should be appreciated that one or more of the components of the electronics subsystem 14 may include a rechargeable battery, and the coupling of the power cable 30 to the external power source may further serve to charge the rechargeable battery, often simultaneously with powering the surgical sponge management system 10. Cord wraps 36 may be coupled to the main support 24, for example, on the rear side 28 near the opening from which the power cable 30 exits, to compactly stow the power cable 30 to the stand 12. A handle 38 may be coupled to the main support 24, for example, on the front side 26, to facilitate maneuvering the surgical sponge management system 10 within the medical facility.

With continued reference to FIGS. 1 and 2, the electronics subsystem 14 includes a module base 40, a display 42, and a data reader 44. The module base 40 may be secured to the stand 12, and more particularly in engagement with the front side 26 of the main support 24. The power connector 34 is electrically coupled to a complementary power port (not shown) on a rear of the module base 40. The module base 40 may include a housing 46, and a mount 48 coupled to the housing 46. It is appreciated that the module base 40 may further include a processor, memory, communications device, and/or other hardware. The mount 48 is configured to be removably coupled with the display 42 such as a tablet displaying a graphical user interface. Likewise, the housing 46 may define a cradle 50 configured to be removably coupled with the data reader 44. The illustrated implementation shows the cradle 50 being a recess to receive and support the data reader 44. With the HCP often engaging the display 42 and the data reader 44, the electronics subsystem 14 is preferably coupled to the main support 24 at an optimal height. For example, the electronics subsystem 14 may be coupled to the main support 24 between the handle 38 and the dispenser assembly 16 such that the display 42 is relatively near eye-level for most adults of average height. For another example, the display 42 may be positioned between four feet and six feet above floor level. Further, a joint between the mount 48 and the module base 40 may provide for selective adjustment of the display 42 in one, two, or three or more degrees of freedom. The joint may be a pivot providing for vertical adjustment of the display 42 relative to the module base 40 to accommodate users of differing heights.

The data reader 44 is configured to be used as either a handheld device or as supported by the cradle 50, and seamlessly transition between the configurations. More particularly, when supported by the cradle 50, the surgical sponges may be brought near the data reader 44 for the data reader 44 to detect unique identification information associated with a tag associated with the surgical sponges. Should it not be feasible to bring the surgical sponges near the data reader 44 or as otherwise desired, the data reader 44 may be efficiently removed from the cradle 50 and actuated near the tag associated with the surgical sponges. In an exemplary implementation, the data reader 44 is an RFID reader configured to detect RFID tags associated with the surgical sponges as described in commonly-owned International Publication No WO2021/041795, published Mar. 4, 2021, and commonly-owned International Publication No WO2021/097197, published May 20, 2021, each of which is hereby incorporated by reference in its entirety. Exemplary tags other than RFID tags are disclosed in commonly-owned International Publication No. WO2017/112051, published Jun. 29, 2017, which is hereby incorporated by reference in its entirety.

The dispenser assembly 16 may be mounted to the main support 24 opposite the base 18 of the stand 12. In other words, the dispenser assembly 16 may sit atop the stand 12. The dispenser assembly 16 and its components to be described provides several advantageous functions, including but not limited to selectively limiting a footprint of the surgical sponge management system 10, providing storage and ergonomic dispensing of sponge sorters 52 from a carton 56 of the sponge sorters 52, providing storage and ergonomic dispensing of surgical draping 53 from a carton 58 of the surgical draping 53, and supporting at least one arm 54 with subcomponents for weighing the surgical sponges disposed within the sponge sorter 52. As used herein, the cartons 56, 58 may be a semi-rigid or rigid container, for example, a box defining an opening, or alternatively may be a flexible container such as a bag defining an opening. The sponge sorters 52 may be stacked, rolled together, or otherwise packaged within the carton 56, and are alternatively referred to herein as counting bags. Further, as used herein, the surgical draping 53 may be in reference to a single surgical drape or multiple surgical drapes. The carton 58 of surgical draping 53 may initially include one, two, three, four, or five or more surgical drapes, which may be stacked, rolled together, or otherwise packaged within the carton 58.

Figure 3:
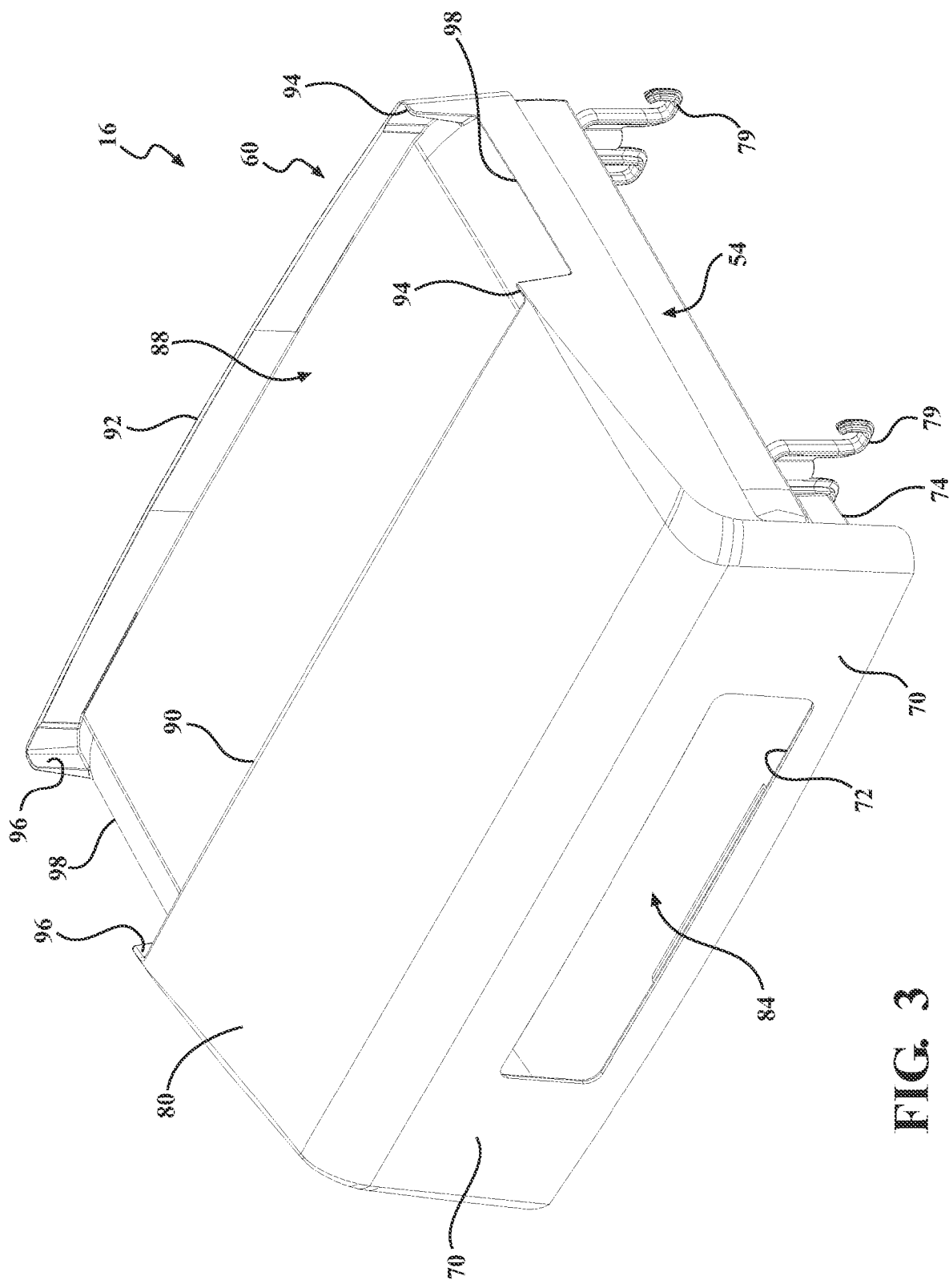
FIG. 3 is a top perspective view of the dispenser assembly.
Figure 4:
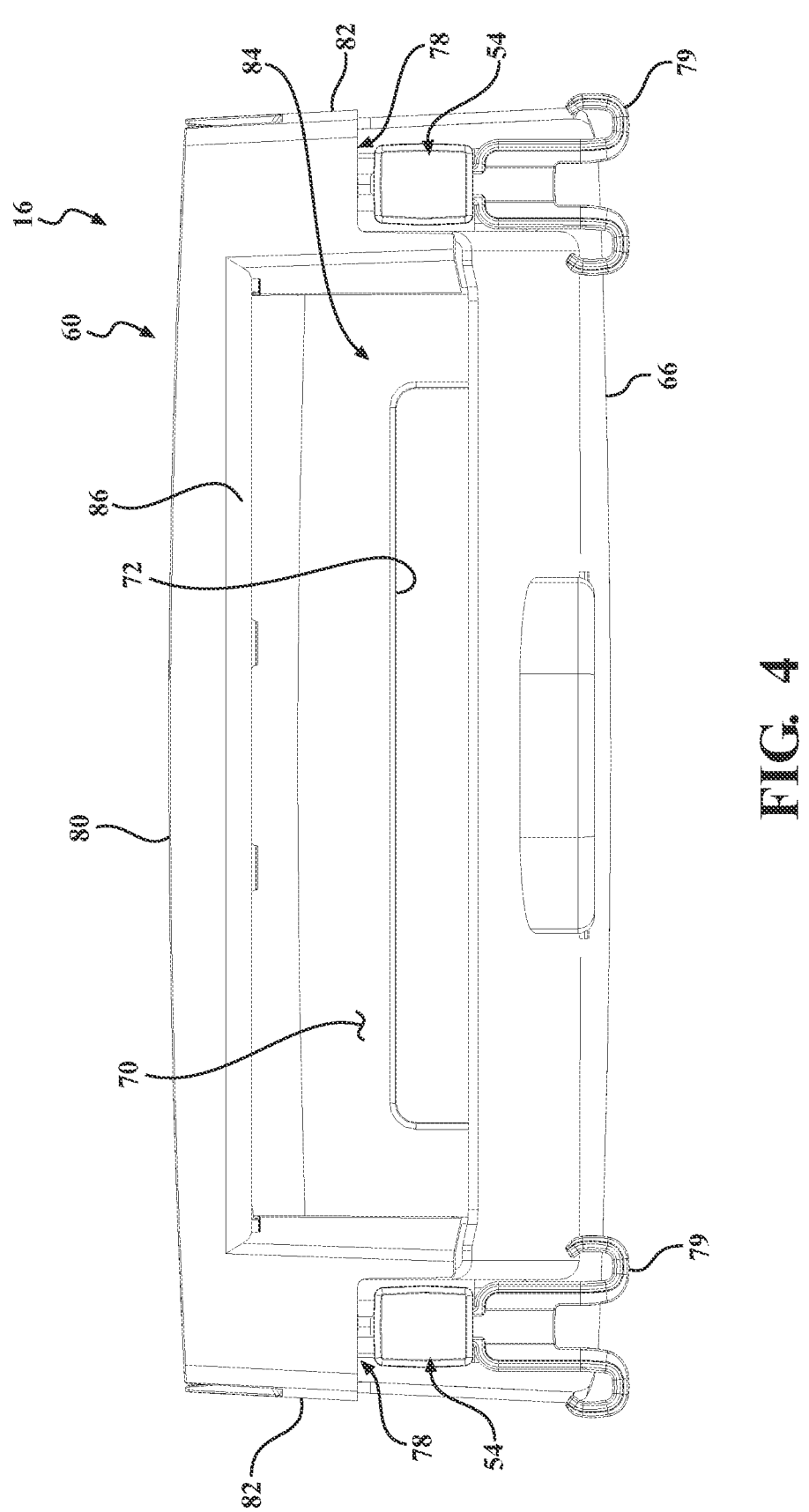
FIG. 4 is a rear elevation view of the dispenser assembly.
Figure 5:
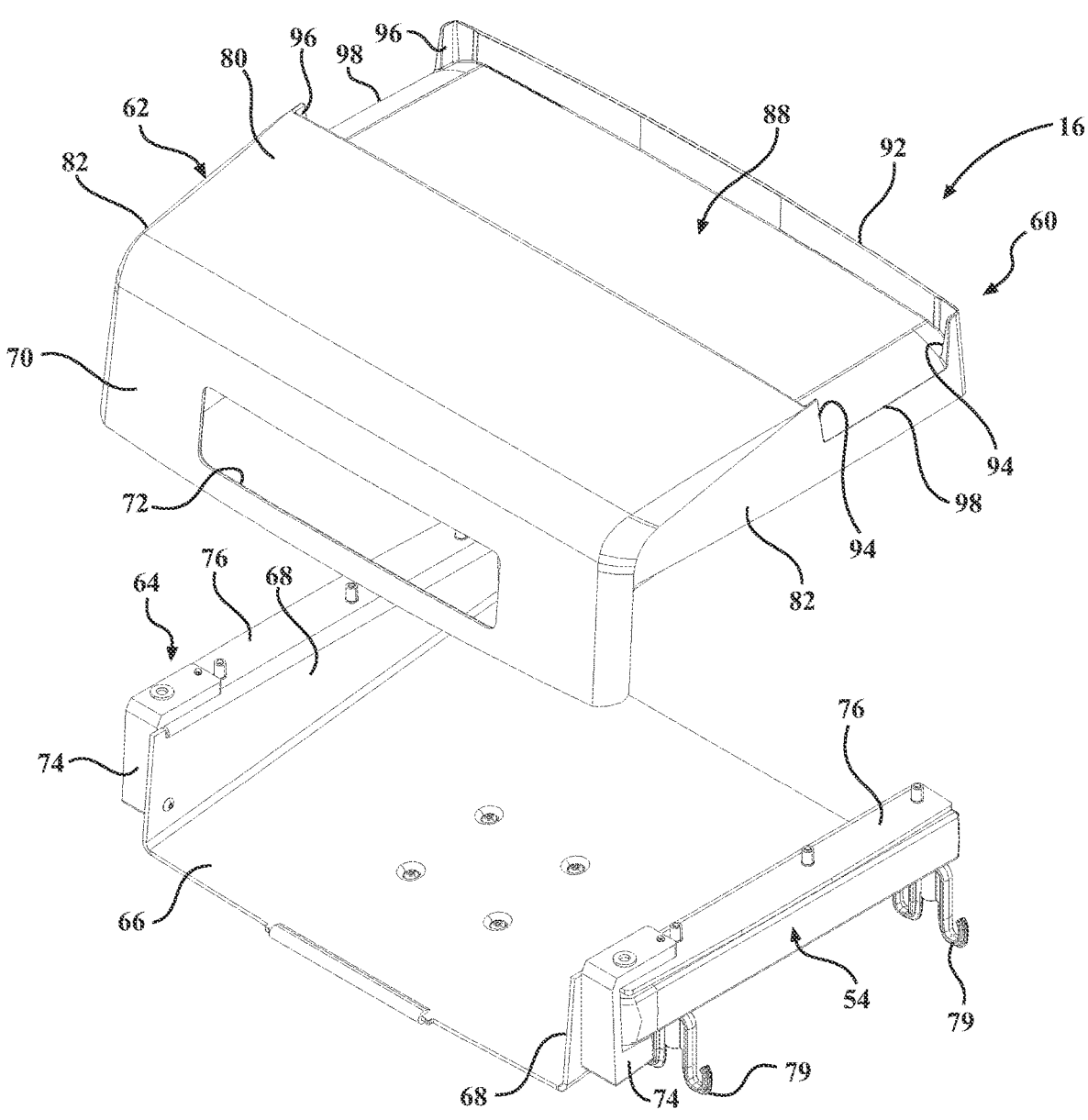
FIG. 5 is an exploded view of the dispenser assembly in which an upper housing is separated from a lower housing.

Referring now to FIGS. 3-5, the dispenser assembly 16 includes a housing 60, which may be comprised of an upper shell 62 coupled to a lower shell 64. The lower shell 64 may be mounted to a complementary mounting flange (not shown) at an upper end of the main support 24. FIG. 5 shows a lower wall 66 of the lower shell 64 defining four holes receiving fasteners for mounting the dispenser assembly 16 to the main support 24. The lower shell 64 may include lower sidewalls 68 extending upwardly from the lower wall 66. As appreciated from a trapezoidal shape of the lower sidewalls 68, the lower wall 66 may slope downwardly from the rear to the front when mounted to the main support 24. As to be further described, the downward slope of the lower wall 66 facilitates the carton 56 of the sponge sorters 52 descending into position inside of a front wall 70 of the dispenser assembly 16, thereby positioning an opening of the carton 56 adjacent and in communication with a front opening 72 of the dispenser assembly 16 for ergonomic dispensing.

The dispenser assembly 16 includes at least one mounting bracket 74 coupled to the housing 60. The mounting brackets 74 couple the arms 54 to the housing 60. As best shown in FIG. 5, the mounting bracket 74 is coupled to outer surfaces of each of the lower sidewalls 68 of the lower shell 64. The lower shell 64 may further include a flanged wall 76 extending outwardly from each of the lower sidewalls 68, and the mounting bracket 74 may be further coupled to the flanged walls 76. The resulting configuration includes the arms 54 being positioned within recesses 78 defined by the flanged walls 76 and the lower sidewalls 68. More particularly, the arms 54 may be pivotably coupled to and extending rearwardly from the mounting brackets 74. The arms 54 are independently and selectively movable between an undeployed position in which the arms 54 are positioned within the recesses 78 (see FIGS. 1 and 3-5), and a deployed position in which the arms 54 extend outwardly beyond the sidewalls of the housing 60 (see FIG. 2). Sorter couplers 79 coupled to the arms 54 are configured to support the sponge sorters 52. The sorter couplers 79 may be at least one hook, for example, the two hooks best shown in FIG. 4, or other suitable retention mechanism such as a clasp, hook-and-eye connection, and the like. Each arm 54 may include at least two sorter couplers 79 configured to cooperatively support two sponge sorters. In alternative implementations, the arms 54 may be configured for rotational movement, linear translation, or telescopic displacement to be deployed.

The upper shell 62 includes the front wall 70, an upper wall 80, and upper sidewalls 82. The walls 70, 80, 82 generally form an L-shaped contoured to the lower shell 64 such that, when coupled to one another, define an internal or first storage location 84. In particular, the upper sidewalls 82 of the upper shell 62 are secured to the lower sidewalls 68 of the lower shell 64, for example, with a fastener, to form the housing 60. Alternatively, it is contemplated that the upper shell 62 and the lower shell 64 may be integrally formed through a suitable manufacturing process such as blow molding, injection molding, three-dimensional printing, or the like, such that the housing 60 is monolithic in construction. In other implementations, the upper shell 62 and the lower shell 64 may be pivotably coupled to one another, for example, with a hinge, so as to permit the upper shell 62 to be pivoted to access the first storage location 84 for cleaning or the like. The housing 60 defines the first storage location 84 between the front wall 70, the upper wall 80, and the sidewalls 68, 82.

The first storage location 84 is sized to receive the carton 56 of the sponge sorters 52. More particularly, the housing 60 defines a rear opening 86 in communication with the first storage location 84, and the front opening 72 in communication with the first storage location 84. The rear opening 86 is larger than the front opening 72. As best shown in FIG. 4, the rear opening 86 may be rectangular in shape, which often is the typical shape of the carton 56 of the sponge sorters 52. The rear opening 86 should be sized slightly greater than the carton 56 so as to permit the user to direct the carton 56 through the rear opening 86 and into the first storage location 84. The user should load the carton 56 into the first storage location 84 such that the dispenser opening of the carton 56 is facing the front opening 72 of the dispenser assembly 16. As mentioned, the lower wall 66 is downwardly sloped to facilitate the user fully loading the carton 56 of the sponge sorters 52 into the first storage location 84. The dispensing opening of the carton 56 is accessible through the front opening 72.

Returning again to FIG. 2, a method of hanging the sponge sorter 52 from the arm 54 of the dispenser assembly 16 includes retrieving the sponge sorter 52 from the carton 56 supported within the first storage location 84 of the dispenser assembly 16. The HCP may approach the surgical sponge management system 10 from the front, and access the carton 56 of sponge sorters 52 through the front opening 72. The HCP may pull or draw one of the sponge sorters 52 from the carton 56 through the front opening 72. The ergonomics of the arrangement advantageously do not require the HCP to, for example, retrieve an object from within a wire basket supported atop a stand. Safety is further promoted since the dispenser assembly 16 is likely at or above head-level. The sponge sorter 52 may be folded or unfolded upon removal from the carton 56. The sponge sorter 52 may be unfolded to assume a configuration shown in FIG. 2. The dispenser assembly 16 may be located above an elevation of the arms 54—i.e., a hanging height of the sponge sorters 52—to prevent or minimize contamination of the carton 56 of the sponge sorters 52. Further, the location of the dispenser assembly 16 being centered atop the main support 24 avoids obstructing upper and lower pockets of the sponge sorters 52. The location and configuration of the dispenser assembly 16 of the present disclosure improves on known devices where a lower positioning of the storage requires the sponge sorters to be hung at a lower hanging height, often requiring the HCP to bend down close to the floor to access the lower pockets. The dispenser assembly 16 avoids the aforementioned shortcoming while accommodating HCPs across a spectrum of heights.

The HCP may suspend or hang the sponge sorter 52 from one of the arms 54. The sponge sorter 52 may include eyelets configured to be directed over hooks of the sorter couplers 79. The step may be performed before or after moving the arm(s) 54 from the undeployed position to the deployed position. In other words, the HCP may hang the sponge sorter 52 on the arm 54 with the arm 54 positioned within the recess 78 adjacent the side of the housing 60. The housing 60 prevents the arm 54 from moving away from the HCP during the installation, which may be ergonomic should the HCP be using both hands to support and align the eyelets and hooks. Alternatively, the HCP may, for example, pivot the arm 54 outwardly, after which the HCP hangs the sponge sorter 52 on the arm 54.

At any time after the sponge sorter 52 is hung from the arm 54, it may be desirable to move the surgical sponge management system 10 about the medical facility. Yet, with the arms 54 deployed, a wingspan of the surgical sponge management system 10 is appreciable, increasing the difficulty of navigating obstructions within the medical facility. The surgical sponge management system 10 advantageously provides for moving the arm(s) 54 from the deployed position to the undeployed position—with one or more sponge sorters already coupled thereto—thereby reducing the wingspan of the surgical sponge management system 10. The reduction in wingspan may be equal to or less than an original footprint of the surgical sponge management system 10. In other words, the sponge sorter 52 that is hung from the arm 54 in the undeployed position is within a projected outer perimeter of the base 18 (i.e., the original footprint). As a result, the surgical sponge management system 10 may be just as maneuverable with one or more sponge sorters 52 already hung and ready to be deployed in service. The HCP may grasp the handle 38 and maneuver the surgical sponge management system 10 as needed.

As previously discussed, the surgical sponge management system 10 includes the electronics subsystem 14, components of which often need to be draped with surgical draping 53 that maintains a sterile barrier. Like the internal or first storage location 84, the dispenser assembly 16 advantageously provides an external or second storage location 88 for on-board storage and ergonomic dispensing of the surgical draping 53. Referring again to FIGS. 1, 3 and 5, the second storage location 88 may be generally defined by a recess within the upper wall 80 of the upper shell 62. Stated differently, the upper shell 62 may include a first retention geometry 90 and a second retention geometry 92 that at least partially form the second storage location 88. In the illustrated implementation, the first retention geometry 90 and the second retention geometry 92 are frames extending widthwise across the housing 60. The first retention geometry 90 and the second retention geometry 92 are spaced apart from one another by a distance preferably slightly larger than the width of the carton 58 of surgical draping 53. As a result, the carton 58 supported within the second storage location 88 may be generally constrained from moving in the forward and rearward directions. The second retention geometry 92 may be contoured with a rear of the housing 60, and the first retention geometry 90 may be positioned at any suitable location along a depth of the housing 60.

The upper shell 62 may further include third retention geometry 94 and a fourth retention geometry 96 that further forms the second storage location 88. In the illustrated implementation, the third retention geometry 94 are frames extending depthwise along one of the upper sidewalls 82 of the housing 60, and the fourth retention geometry 96 are frames extending depthwise along the other one of the upper sidewalls 82 of the housing 60. The third retention geometry 94 and the fourth retention geometry 96 are spaced apart from one another by a distance preferably slightly larger than the length of a carton 58 of surgical draping 58. The carton 58 supported within the second storage location 88 may be generally constrained from moving in the lateral directions.

The third retention geometry 94 and/or the fourth retention geometry 96 may define a slot 98. The slot 98 facilitates ergonomic dispensing of the surgical draping 53 from the carton 58. As best shown in FIGS. 1 and 2, a dispenser opening of compatible cartons may be defined on a lower aspect of the shortest side. The dispenser opening is aligned with the slots 98 when the carton 58 of the surgical draping 53 is supported in the second storage location 88. For example, with a small portion of the surgical draping exposed through the dispenser opening (by virtue of removal of the previous surgical draping), the HCP may simply pull or draw outwardly (and downwardly) to dispense the surgical draping 53. The carton 58 of the surgical draping 53 is prevented from ejecting from the second storage location 88 by the third retention geometry 94 or the fourth retention geometry 96. Similar to the first storage location 84, the ergonomics of the second storage location 88 advantageously do not require the HCP to, for example, pull upwardly. The surgical draping 53 may be unfolded or unfurled, and draped over the electronic subsystem 14 and/or other components as needed. For example, FIG. 1 shows the surgical draping 53 covering the data reader 44 with a closure device.

It is further appreciated that the first storage location 84 and the second storage location 88 facilitate ease with removal and replacement with their respective cartons 56, 58. Once the carton 56 of the sponge sorters 52 is empty, the rear opening 86 facilitates ease with removal and replacement with another carton 56. Likewise, once the carton 58 of the surgical draping 53 is empty, the carton 58 may simply be lifted by a small distance for removal, and another carton 58 may be positioned within the second storage location 88. The reverse configuration is contemplated in which the first storage location 84 is associated with the carton 58 of the surgical draping 53, and the second storage location 88 is associated with the carton 56 of the sponge sorters 52.

The dispenser assembly 16 of the present disclosure advantageously facilitates locating most or all of the accessories of the surgical sponge management system 10 near the display 42 or the data reader 44 in compact and space-conscious manner. The compactness is realized by the first storage location 84 being "internal" to the housing 60 of the dispenser assembly 16, and the second storage location 88 being "external" to the housing 60. Internal may be considered most of the carton not extending beyond the housing 60, and external may be considered most of the carton extending beyond the housing or exposed in an unobstructed manner. Of course, subtle modifications in geometry and minor changes in arrangement of the cartons relative to the housing 60 may be considered within the scope of the present disclosure. In one alternative implementation, for example, the housing 60 of the dispenser assembly 16 may not define the rear opening 86, and the upper wall 80 of the upper shell 62 may define an opening positioned forward of the second storage location 88 and in communication with the first storage location 84. The carton 56 of the sponge sorters 52 may be directed through the opening and into the first storage location 84 to be accessible through the front opening 72.

As mentioned, the surgical sponge management system 10 may facilitate estimating blood loss associated with the surgical sponges in a seamless workflow, and more particularly, in a seamless workflow with the checking or counting out of the surgical sponges. In other words, the user may count out the surgical sponges using the data reader 44 and deposit the surgical sponge(s) (S) into one of the pockets of the sponge sorter 52 (see FIG. 2). Without any further action necessitated by the user, the surgical sponge management system 10 may be configured to weigh the surgical sponge (and the sponge sorter 52), correlate the change in weight to the surgical sponge that was counted out, subtract a dry weight associated with a type of the surgical sponge, estimate the blood absorbed by the surgical sponge, and update the estimated blood loss on the display 42. To facilitate the weighing of the surgical sponges, the arm(s) 54 may include a weighing means. Additional advantages realized by integrating the weighing means on the arm 54 will also be described in further detail.

Figure 6:
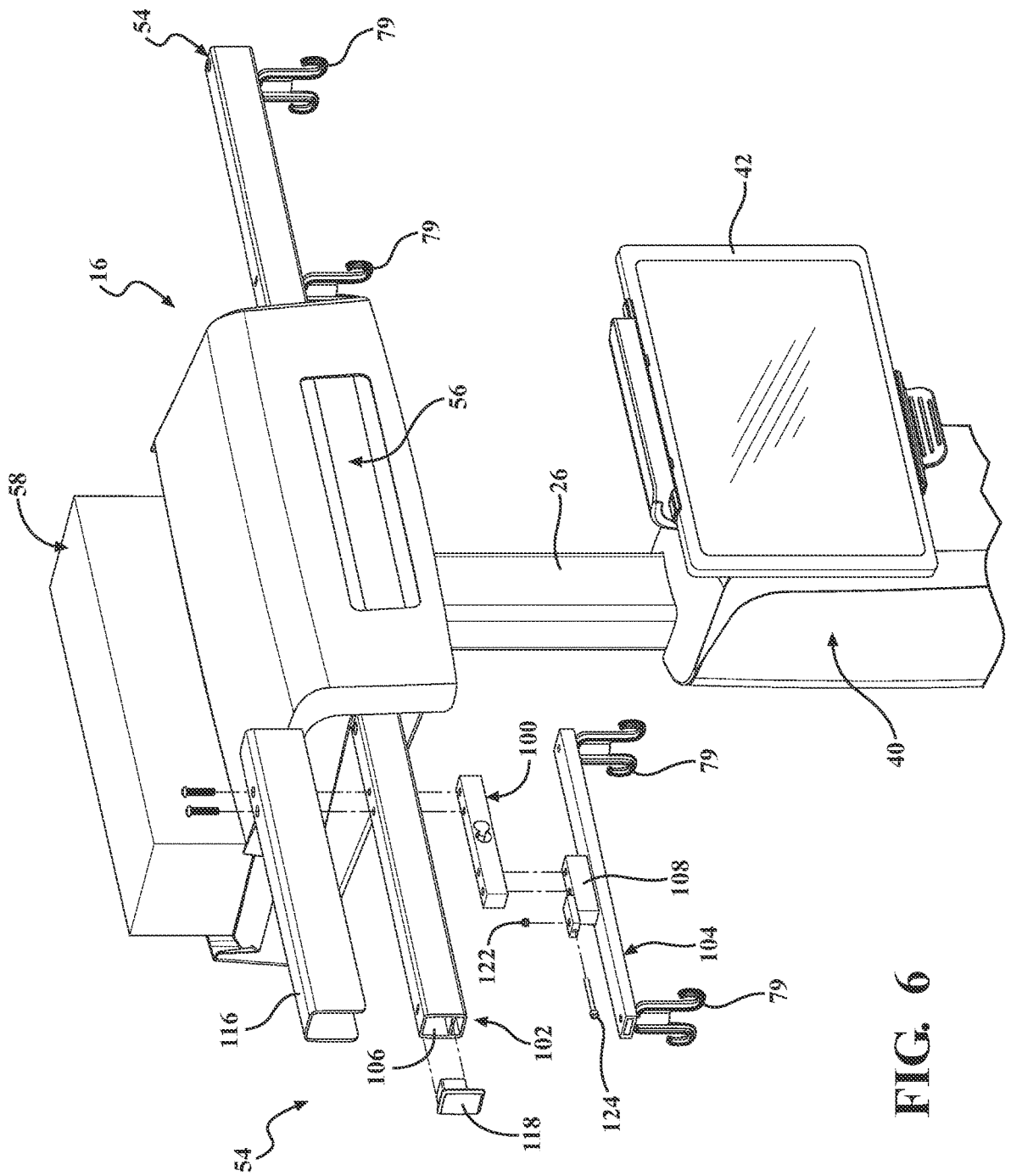
FIG. 6 is a perspective view of a portion of the system with one of the arms shown as exploded and including a beam, a loading bar, and a load cell for detecting a measured weight of the sponge sorter and the surgical sponges.
Figure 7:
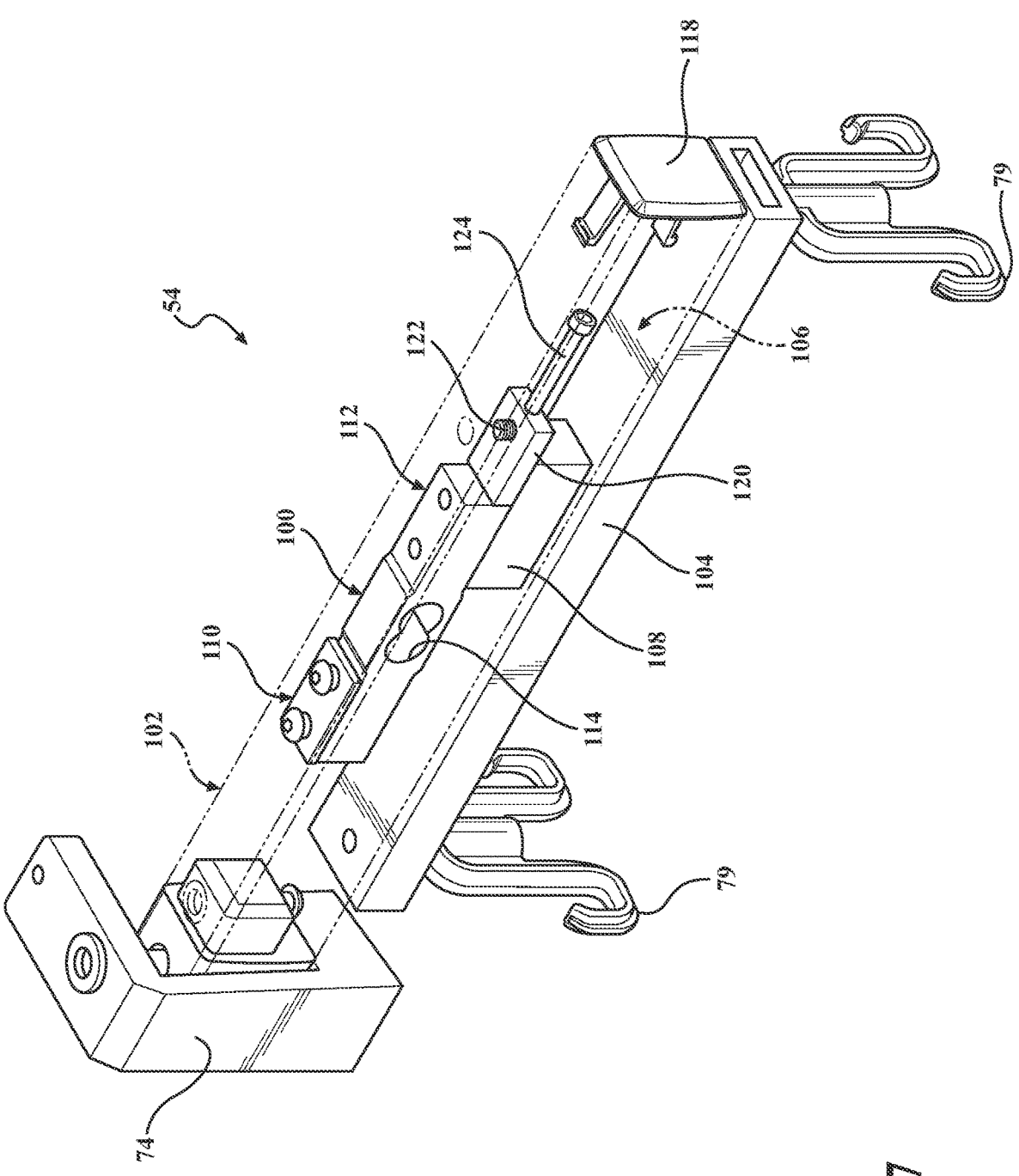
FIG. 7 is a top perspective view of the arm of FIG. 6 with the beam illustrated as transparent to show the load cell and other subcomponents of the arm disposed within the beam.

Referring now to FIGS. 6 and 7, the arm 54 includes the weighing means, a beam 102, and a loading bar 104. The weighing means may be a load cell 100, and other suitable means for weighing objects that are supported from the arm 54 are contemplated. The beam 102 is coupled to the housing 60 of the dispenser assembly 16 with the mounting bracket 74, and the sorter couplers 79 are coupled to the loading bar 104. The load cell 100 couples the loading bar 104 to the beam 102 such that a mass applied to the loading bar 104 is measurable by the load cell 100. In other words, the loading bar 104 and beam 102 may not be coupled to one another except with the load cell 100 such that an entirety of the mass supported by the arm 54 is measurable by the load cell 100. In most instances, the mass is the sponge sorter 52 suspended from the arm 54, and any surgical sponges or objects received therein.

The arm 54 is pivotably coupled to the housing 60 to provide for the aforementioned functionality of being movable between the undeployed and deployed positions. As a result, the arm 54 may be cantilevered; i.e., supported at or near one end with the mounting bracket 74 and unsupported at the other end. With appreciation for the structural mechanics of cantilevers, the load cell 100 may be a bending beam load cell. The bending beam load cell advantageously provides for accurate and repeatable measurements with a small form factor concealable within the arm 54. The load cell 100 may be selected from the group consisting of a bending beam load cell, double bending beam load cell, shear beam load cell, S-type load cell, canister load cell, torsion load cell, spoke type load cell, ring torsion load cell, a load pin, and strain gauge. One exemplary double-bending beam load cell is sold under the tradename DF2SR-3 by HBK Inc. (Marlborough, Mass.).

Figure 8:
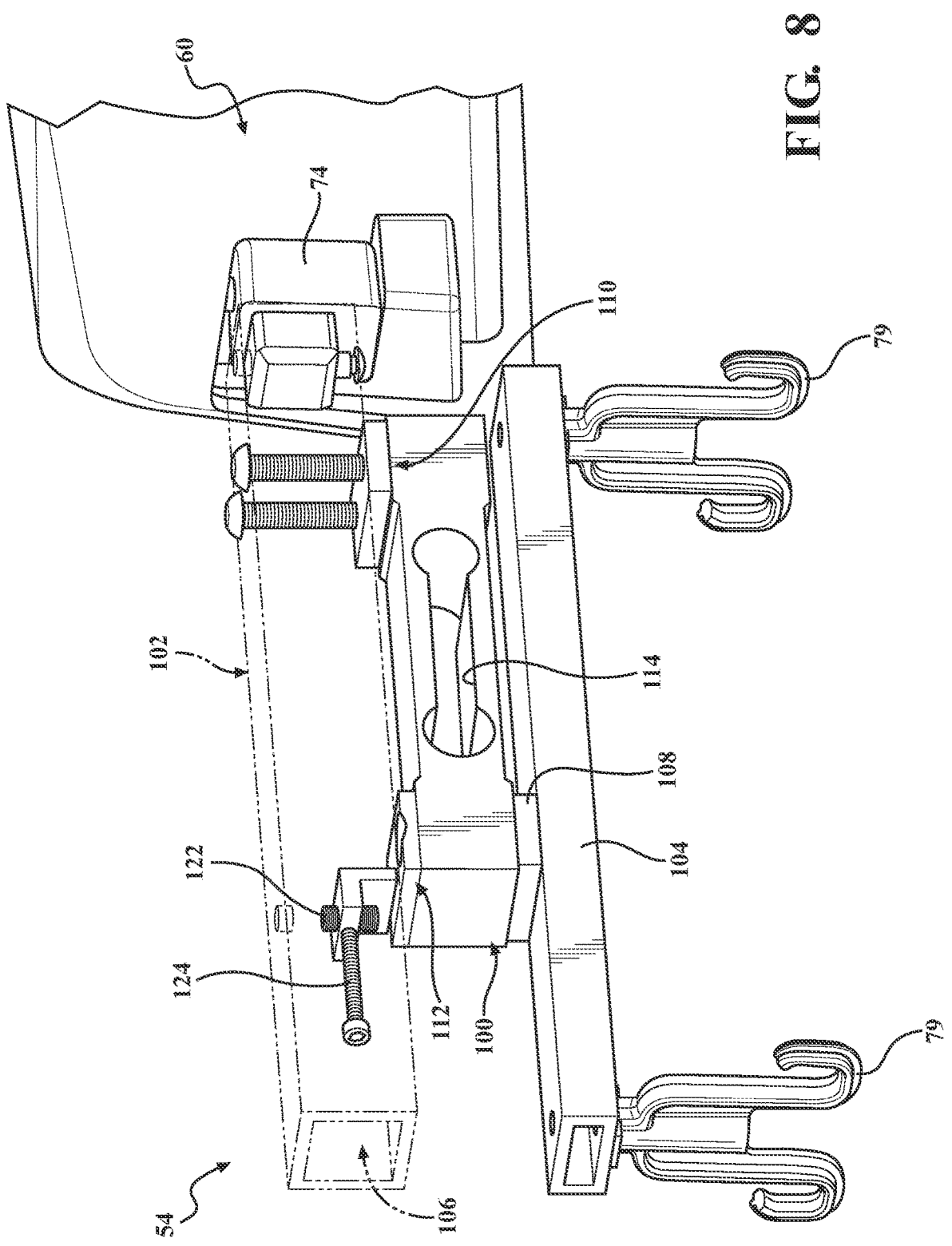
FIG. 8 is a top perspective view of another implementation of the arm in which the load cell is positioned external to the beam.

With continued reference to FIGS. 6 and 7, the beam 102 may define a channel 106, and the load cell 100 may be disposed within the channel 106. In one example, the beam 102 is formed from an extrusion to define the channel 106 being square or rectangular in cross section, but other suitable geometries are contemplated. The channel 106 may be sized to accommodate the load cell 100 and other subcomponents of the arm 54 such as a mounting block 108. A first portion or end 110 of the load cell 100 may be fixedly secured to the beam 102, and a second portion or end 112 of the load cell 100 may be fixedly secured to the loading bar 104. As best shown in FIG. 7, the first end 110 of the load cell 100 is secured to an upper surface of the beam 102 with fasteners. The second end 112 of the load cell 100 is secured to the mounting block 108, which itself is secured to the loading bar 104. The mounting block 108 may be disposed within the channel 106, whereas the loading bar 104 may be disposed outside of the channel 106. An opening 114 of the load cell 100 may delineate between the first portion 110 and the second portion 112. Objects supported by the loading bar 104 result in a downward force on the mounting block 108 and the second end 112 of the load cell 100. The downward force causes deflection of the load cell 100 that is measurable with a strain gauge or other suitable transducer. Owing to the dimensions and material of the load cell 100 as well as the characteristics of the opening 114, the measured deflection is indicative of the load. The deflection is converted into an electric signal that is transmitted to the processor of the electronics subsystem 14. A cover 116 and an end cap 118 may be provided to seal or conceal within the beam 102 the subcomponents of the arm 54. Therefore, design of the beam 102 itself protects the load cell 100 by being disposed within the channel 106. Alternatively, FIG. 8 shows an implementation of the arm 54 in which the certain subcomponents are disposed within the channel 106, but the load cell 100 is disposed external to the beam 102. The implementation of FIG. 8 shows the first end 110 of the load cell 100 coupled to an underside of a lower surface of the beam 102. Such an arrangement may be particularly well suited for designs requiring a larger weighing means; i.e., the load cell 100 is too large to be disposed within the channel 106. A suitable cover may be provided to house the load cell 100, the beam 102, and the like.

To further ensure accurate measurements and avoid damaging the load cell 100, the arm 54 may include a load limit plate 120 fixedly secured to the mounting block 108. A gap adjustment screw 122 is threadedly coupled to the load limit plate 120. The gap adjustment screw 122 has a stop end (not shown) and is selectively moveable relative to the load limit plate 120. The gap adjustment screw 122 can be adjusted to a position such that the stop end prevents further load from being applied to the load cell 100 if the weight on the loading bar 104 exceeds a predetermined maximum weight. For example, the gap adjustment screw 122 may be selectively adjusted so as to bottom out on a lower inner surface of the beam 102 (or other designated structure) if the load applied to the load cell 100 exceeds the predetermined maximum weight. A set screw 124 may be provided to fix the gap adjustment screw 122 in the desired position corresponding to the predetermined maximum weight. In other words, the load limit plate 120, the gap adjustment screw 122, and the load cell 100 can be calibrated to the predetermined weight. During calibration, a mass of a known weight (e.g., twenty pounds) may be applied to the loading bar 104 and the gap adjustment screw 122 can be adjusted abut the lower inner surface of the beam 102. The mass is removed, and the set screw 124 may be tightened. Subsequent during operation, it can be assumed that the gap adjustment screw 122 would again bottom out should twenty pounds be supported by the arm 54.

The weighing means is in communication with the processor (not identified), which may be disposed within the module base 40. Alternatively, the weighing means may be in wireless communication with a remote processor such that processing steps to be described may be performed remotely and returned wirelessly to be displayed on the display 42. The processor may include non-transitory computer-readable medium storing instructions configured to be executed to perform the methods disclosed herein. The instructions may be provided on a computer program product. The weighing means is configured to detect a measured weight of the objects supported by the arm 54, most often the sponge sorter 52 and the surgical sponges disposed within the pockets of the sponge sorter 52. The measured weight, or a corresponding signal or data indicative of the measured weight, is transmitted to the processor.

In a typical surgical procedure in which a surgical sponge is utilized, the surgical sponge is checked or counted in to be used during the surgical procedure. The surgical sponge may include a tag, such as the RFID tag previously described. With reference to FIG. 9, an exemplary method 130 may include counting in the surgical sponge by causing the tag to be detected by the data reader 44 (step 132). The RFID tag includes identifying data from which the processor is configured to determine a type of the surgical sponge, in which case the surgical sponge may be considered a compatible surgical sponge to be further described. Exemplary types of surgical sponges are a 4×4 gauze and an 18×18 lap sponge. The features of the surgical sponge management system 10 also account for articles that may not be automatically identified based on the tag, hereinafter referred to as fluid-absorbing articles. The compatible surgical sponges, the fluid-absorbing articles, the sponge sorters 52, and other objects may collectively be referred to as "items." The type of the surgical sponge is associated with a dry weight that is stored in memory. The dry weight may be an average weight based on empirical, manufacturing, or other data associated with the type of the surgical sponge. Based on the data reader 44 detecting the tag, the processor may index a counter of the quantity of surgical sponges to be used during the surgical procedure. The counter may be displayed on the display 42 (see FIG. 13B). The processor may further add the dry weight to the dry weights of previous surgical sponges that were previously been counted in to be used. This may be repeated as many times as necessary based on the anticipated or actual sponge needs of the surgical procedure. The surgical procedure commences or continues as planned.

Either during or after the surgical procedure, the surgical sponges—used and unused—are checked or counted out. The tags of the surgical sponges are again positioned to be detected by data reader 44 to identify the surgical sponges as being counted out to no longer be used during the surgical procedure (step 134). The processor may index the counter accordingly (e.g., subtract by one from the previous quantity), and display on the display 42 the quantity indicative of the surgical sponges that remain counted in (see FIG. 13B). Typically in practice, the user, after confirming on the display 42 the surgical sponge has been counted out, immediately places the surgical sponge in one of the pockets of the sponge sorter 52 (see FIG. 2).

Owing to the integration of the weighing means with the arm 54 of the surgical sponge management system 10, the placing of the surgical sponge in the sponge sorter 52 is automatically detected or sensed as a change in the measured weight by the weighing means (step 136). The measured weight and/or the change in the measured weight is transmitted to the processor. The processor is configured to determine a fluid weight of the fluid absorbed by the surgical sponge based on the measured weight (or the change in the measured weight) and the dry weight of the surgical sponge identified by the data reader as being counted out. In other words, the processor recognizes the type of surgical sponge that was counted out based on the tag detected by the data reader 44, and correlates from the memory the dry weight for that type of surgical sponge. The dry weight is subtracted from the change in the measured weight to equal the fluid weight for the surgical sponge that was counted out (step 138). The fluid weight for each one of the surgical sponges may be logged and stored in the memory for later review and input. With an approximate conversion of 0.994 grams of fluid being equal to one milliliter of blood (or another suitable approximation), the processor estimates blood loss associated with the surgical sponge based on the fluid weight (step 140). The processor transmits the data to be displayed on the display 42 (step 142)(see FIG. 13A). It should be readily appreciated that the aforementioned functionality advantageously obviates the need for the user to determine, recall, and/or manually enter the quantity of each type of surgical sponge that is being counted out before the estimated blood loss may be determined. The need to transport the surgical sponges to a separate scale for weighing is likewise obviated. Moreover, the surgical sponge management system 10 provides the estimated blood loss without any increase in footprint within the surgical suite. The aforementioned steps may be perform automatically and in real-time without requiring the user to alter the workflow of counting in and counting out surgical sponges to which HCPs have become accustomed. In alternative implementations to be described, it is contemplated that the display 42 may provide the user with the option to manually enter or edit the type of surgical sponges that have been counted in and counted out, in which case the processor may automatically update the estimated blood loss based on the entered or edited inputs. It is further contemplated the display 42 may provide the user with the option to manually enter or edit an estimation of non-blood fluids (e.g., amniotic fluid), and/or exclude the surgical sponges with only non-blood fluids.

Another exemplary method 150 includes more than one type of surgical sponge being used in the surgical procedure. Referring to FIG. 10, the data reader 44 detects the tags on a first type of the surgical sponges, and detects the tags on a second type of the surgical sponges (step 152). The first type has a first dry weight that is stored on the memory and the second type has a second dry weight that is stored on the memory. For example, the first type may be 4×4 gauzes and the second type may be 18×18 lap sponges with the lap sponges being heavier than the gauzes. The processor indexes the counter to identify the first type and the second type of the surgical sponges as being counted in to be used during the surgical procedure (step 154). In other words, the processor tracks how many of each of the gauzes or the lap sponges have been counted in.

Later in the surgical procedure, the data reader 44 detects again at least one of the tags to be counted out. The processor further indexes the counter to identify at least one of the first type of the surgical sponges or at least one of the second type of the surgical sponges as being counted out to no longer be used during the surgical procedure (step 156). For example, six of eight of the gauzes that were counted in may have since been counted out, and three of eight of the lap sponges that were counted in may have since been counted out. With the surgical sponges disposed in the sponge sorter 52, the weighing means senses the measured weight (step 158). The processor determines the fluid weight of the surgical sponges based on the measured weight and the dry weights of the surgical sponges identified as being counted out by the counter. In the present example, the processor subtracts—from the measured weight—six times the dry weight of the gauze and three times the dry weight of the lap sponge. The processor estimates the blood loss based on the fluid weight of the surgical sponges (step 164), and transmits to the display 42 data to display the estimated blood loss (step 166). Again, the user need only count out the surgical sponges in a familiar manner and the estimated blood loss may be updated in real-time. Further, the gauzes and the lap sponges, for example, need not be counted out in any particular order or grouping, as the processor indexes the counter accordingly.

The weighing means senses the weight of the objects supported by the arm 54, which includes the sponge sorter 52 itself in addition to the surgical sponges disposed therein. Therefore, the method may include taring the weight to compensate for a tare weight of the sponge sorter 52. In one example, the weighing means may detect the tare weight being equal to below a predetermined magnitude. In other words, it may be empirically established that the tare weight of an empty sponge sorter is below the predetermined magnitude, whereas the surgical sponges—used and unused—are above the predetermined magnitude. In response to the user hanging the sponge sorter 52 on the arm 54, the weighing means senses the change in the measured weight. If the change in the measured weight is equal to or below the predetermined magnitude, the processor determines that the object causing the change in the measured weight is the sponge sorter 52. In another example, the user may provide an input to the display 42 to tare the weighing means with the sponge sorter 52 supported by the arm 54. The processor associates the measured weight, at the instant of the user input, to be the tare weight. After performing subsequent steps of the methods previously described, the processor determines the fluid weight of the surgical sponge(s) based on a calculated difference between the measured weight, and the dry weight(s) and the tare weight.

Figure 11:
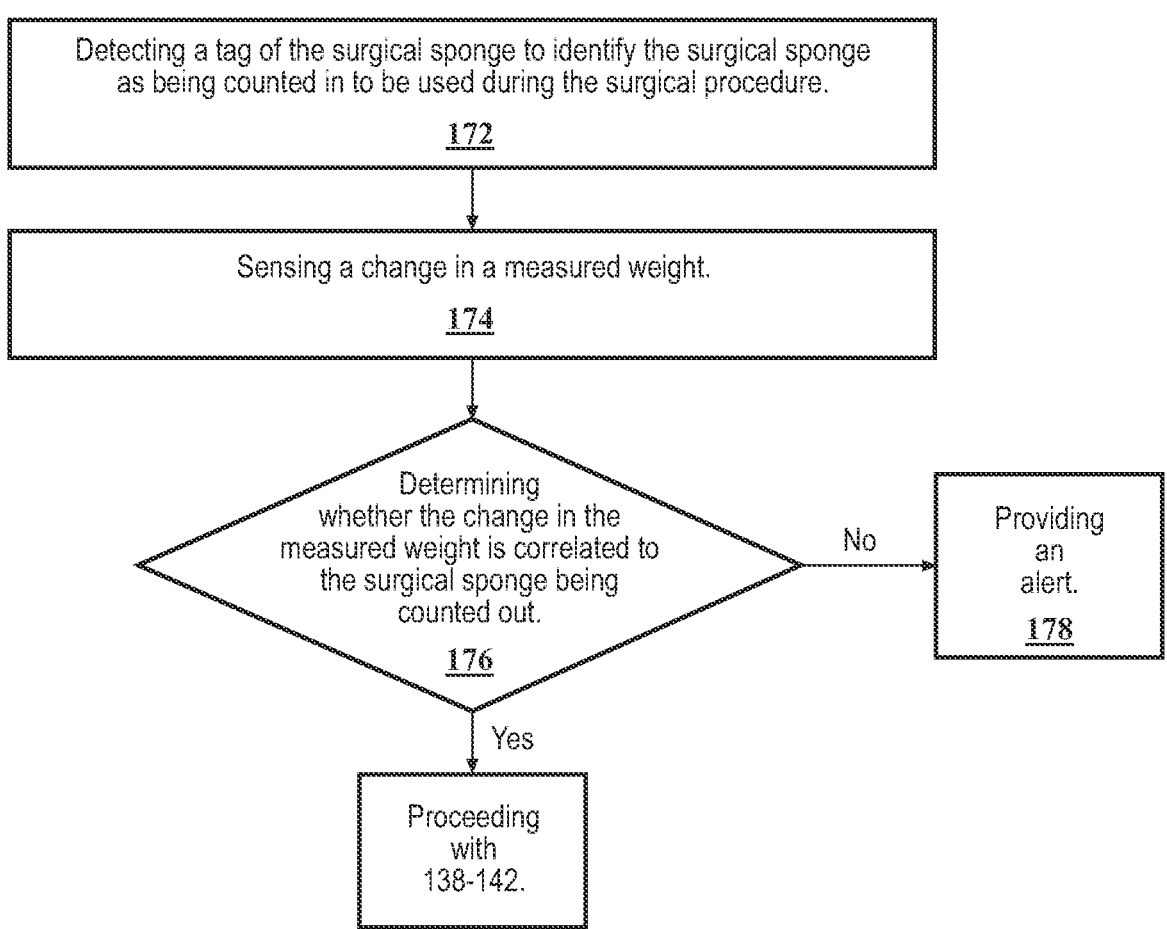
FIG. 11 is still another method of estimating blood loss with the system.
Figure 12:
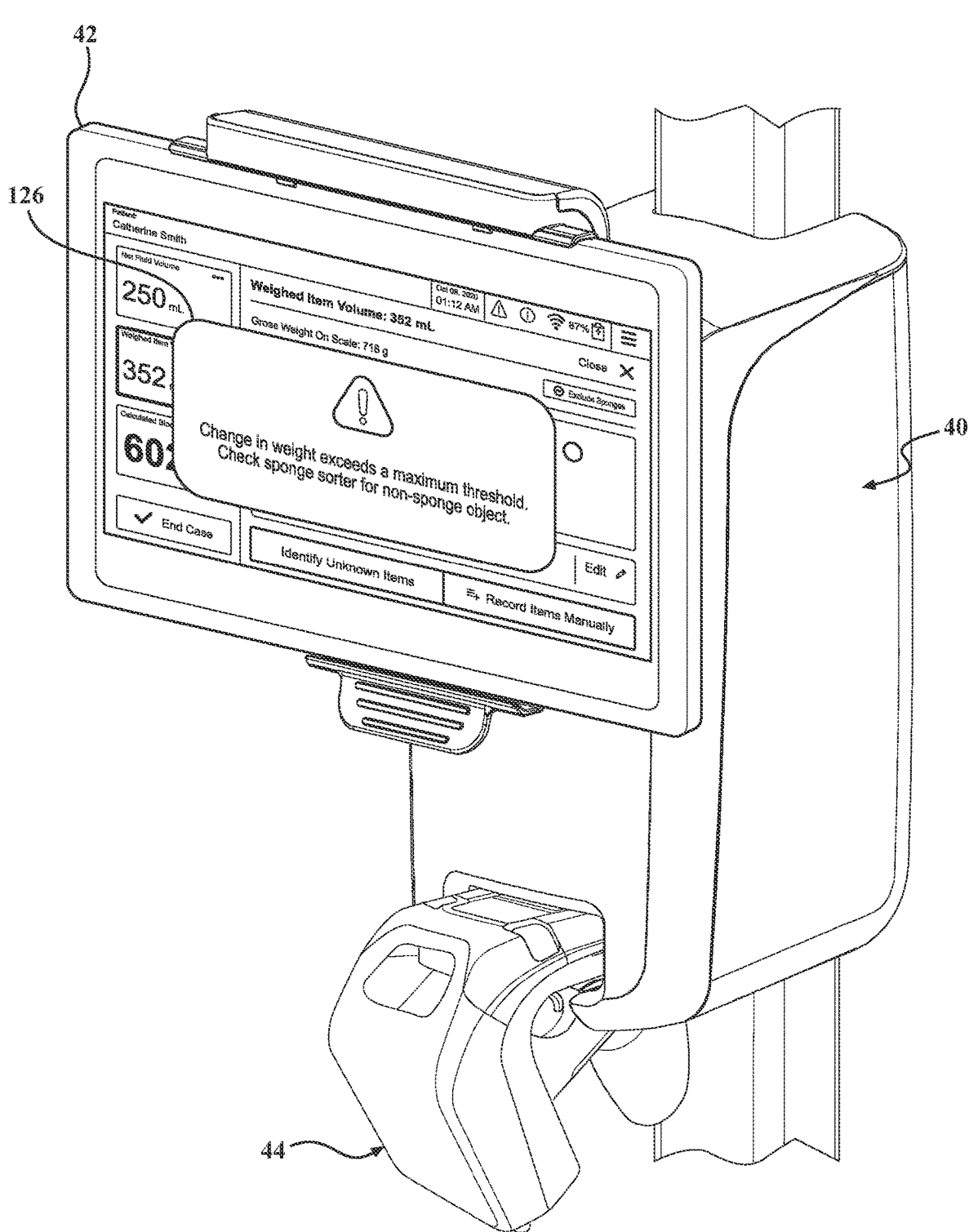
FIG. 12 is a perspective view of a portion of the system in which an alert is provided on a display. The alert may indicate that a change in measured weight detected by weighing means is not correlated to the surgical sponge being counted out.

As mentioned, integrating the weighing means onto the surgical sponge management system 10 provides several advantages in addition to real-time estimation of blood loss, including but not limited to, ensuring the surgical sponge being counted out is actually disposed in the sponge sorter 52 (and not another surgical sponge), and avoiding non-sponge objects being placed in the sponge sorter 52. Referring to FIG. 11, an exemplary method 170 includes detecting, with the data reader 44, the tag of the surgical sponge to identify the surgical sponge as being counted in to be used during the surgical procedure (step 172). The weighing means senses the change in the measured weight in the manner previously described (step 174). The processor determines whether the change in the measured weight is correlated to the surgical sponge being counted out (step 176). If the change in the measured weight is not correlated to the surgical sponge being counted out, an alert 126 (see FIG. 12) may be providing on the display 42 (step 178).

To determine whether the change in the measured weight is correlated to the surgical sponge being counted out, the processor may identify if no previous or subsequent detection of the tag has occurred. In other words, the weighing means senses the change in the measured weight without a surgical sponge being counted out. Such a situation may arise if the user forgets to cause the tag to be detected by the data reader 44 prior to depositing the surgical sponge in the sponge sorter 52. Additionally or alternatively, the processor may compare a measured duration against a maximum duration between the detection of the tag of the surgical sponge and the change in the measured weight. As mentioned, typically the user immediately places the surgical sponge in the sponge sorter 52 after the surgical sponge is counted out. If the maximum duration—for example, ten, twenty, or thirty seconds—has elapsed before the weighing means detects the change in the measured weight, the processor may be configured to not correlate the change in weight with the tag most recently detected by the data reader 44. Stated simply, it may be less likely that a surgical sponge placed in the sponge sorter 52 is the same as the surgical sponge that was counted out, e.g., sixty seconds earlier. Instead, the processor may provide the alert 126 on the display 42 for the user to again count out the surgical sponge as verification, or provide a confirmatory user input to the display 42 or the like. Additionally or alternatively, the processor may compare the change in the measured weight against a preset maximum sponge weight indicative of a blood-saturated sponge. In other words, the memory may store empirical data indicative of the maximum weight achievable by a surgical sponge that is fully saturated with blood or non-blood fluids. The change in measured weight being greater than the preset maximum sponge weight may be indicative of a non-sponge article being received in the sponge sorter. The processor may then not use the measured weight for the estimation of the blood loss. For example, FIG. 2 shows a non-sponge object (O) being disposed in one of the pockets of the sponge sorter 52. Further, the alert 126 may be provided on the display 42 with this particular alert represented in FIG. 11. Lastly, the processor may compare the change in the measured weight against a preset minimum sponge weight. If the change in the measured weight is below the preset minimum, the processor may then not correlate the change in the measured weight for estimation of blood loss. The change in measured weight being less than the preset minimum sponge weight may be indicative of (i) a small, non-sponge article being received in the sponge sorter, (ii) a sponge type being received in the sponge sorter 52 that is smaller than the surgical sponge being counted out, (iii) a surgical sponge or article being removed from the sponge sorter 52 while another surgical sponge or article was added, and (iv) inadvertent movement or support of the sponge sorter 52, such as the sponge sorter being partially supported by surgical stand or the like. If, by contrast, the processor correlates the change in the measured weight to the surgical sponge being counted out, the processor may proceed with the remaining steps of the method described herein, namely determining the fluid weight of the surgical sponge based on the measured weight and the dry weight, estimating the blood loss associated with the surgical sponge based on the fluid weight, and facilitating the display of the estimated blood loss.

In certain implementations, the processor may also be configured to compare the measured weight against a preset maximum load weight; i.e., a maximum weight configured to be safely supported by the arm 54 while ensuring accurate operation of the surgical sponge management system 10. The preset maximum load weight may be selectively tuned to avoid damage to the load cell 100 and/or prevent tipping of the surgical sponge management system 10. If the weight as measured by the weighing means exceeds the preset maximum load weight as determined by the processor, the alert 126 may be provided on the display 42.

Figure 13A:
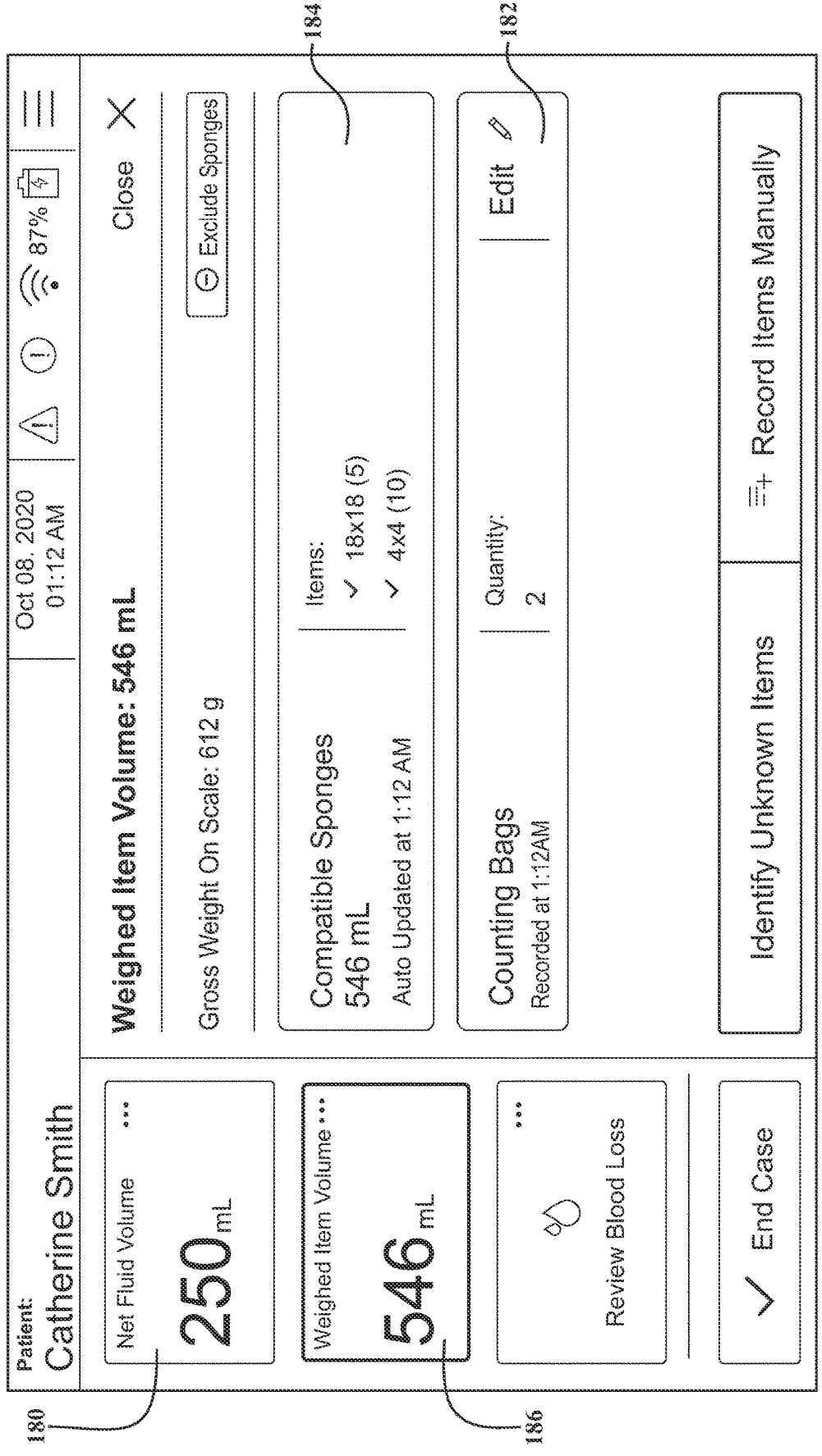
FIGS. 13A and 13B are graphic user interface (GUI) screenshots of a workflow for estimating blood loss with the system.
Figure 13B:
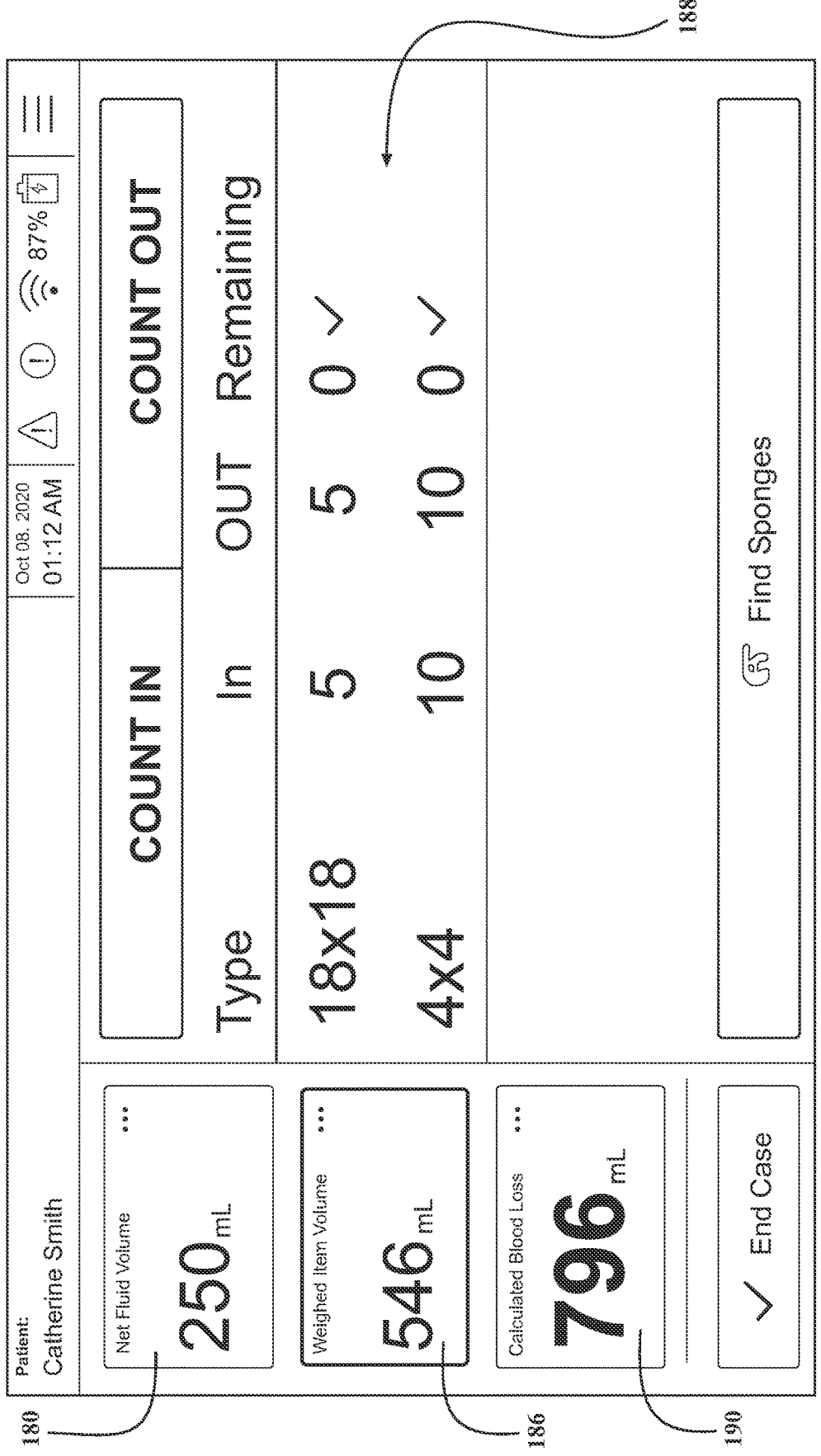

Integrating the weighing means with the surgical sponge management system 10 further provides for efficient sponge management workflows by being managed on a software-based a graphical user interface (GUI) being displayed on the display 42. The display 42 may be a touchscreen display providing a user interface for user input. FIGS. 13A and 13B represent GUI screenshots of a workflow in which the surgical sponges that are being counted in, counted out, and weighed are known to the surgical sponge management system 10. In other words, the tags associated with the compatible surgical sponges include the identifying data from which the processor automatically determines the type of the surgical sponge, for which the dry weight is stored on the memory. Exemplary compatible surgical sponges are sold under the tradenames SurgiCount Safety Sponges or SurgiCount Sponges by Stryker Corporation (Kalamazoo, Mich.). Conversely, and as to be described, the workflows are further able to compensate for sponges and/or other fluid-absorbing articles that do not have tags or whose tags that are unreadable or associated with incompatible surgical sponges.

The GUI screenshots include various tiles and information to be described that are intuitively arranged on the display 42. The GUI screenshots will be described in the context of the specific numerical values and article types displayed thereon, but it should be readily appreciated that these are merely for explanatory purposes. FIG. 13A includes a tile 180 displaying a net fluid volume of the fluid collected during the surgical procedure that is not absorbed by the surgical sponges or the other fluid-absorbing articles. The net fluid volume may be manually entered or captured by other means. The net fluid volume may include irrigation fluid, amniotic fluid, or the like, which may be mixed with blood. The net fluid volume may be visually observed by viewing a V-drape following childbirth, on a display of a surgical suction system, or by other means. The net fluid volume may be obtained by using a system sold under the tradename Triton by Gauss Surgical Inc. (Menlo Park, Calif.).

The GUI screenshot includes a tile 182 displaying the quantity and recorded date and time of the counting bags (e.g., the sponge sorters 52). The tare weights associated with the counting bags may be stored on the memory. As mentioned, the processor may be configured to automatically determine the counting bag being supported on the arm 54 based on the weight of the counting bag matching or not exceeding the predetermined magnitude. The GUI screenshot also includes a tile 184 for displaying data associated with the compatible surgical sponges. With concurrent reference to FIG. 13B, the GUI screenshot includes a count status field 188 including the counter for each type of the surgical sponges used or being used during the surgical procedure. FIG. 13B represents that each of five 18×18 lap sponges and each of ten 4×4 gauzes were previously counted in and have been since counted out with the data reader 44. The count status being automatically updated with the tag being detected by the data reader 44 is indicative that the surgical sponges are compatible surgical sponges.

The count status is also reflected in the tile 184 of FIG. 13A. In particular, the tile 184 includes the type and the quantity of the surgical sponges, and an indicia showing all of the surgical sponges have been counted out. Based on the gross weight sensed by the weighing means and the tare weight of the counting bags, the fluid weight of the compatible surgical sponges is determined. Based on the fluid weight of the compatible surgical sponges, the estimated blood loss associated with the surgical sponges is determined and displayed in the tile 184. The information displayed in tile 186 may be more prominently displayed or visually emphasized. In the example of FIGS. 13A and 13B, the compatible surgical sponges are the only objects being weighed, and therefore the estimated blood loss displayed in tile 186 matches the estimated blood loss displayed in tile 184. Once the user has completed the process or as otherwise desired, the estimated blood loss may be calculated or recalculated, and displayed in tile 190. The columnar arrangement of tiles 180, 186, 190 intuitively appears as mathematical problem formatting easily recognizable to the user.

FIGS. 14A-14D represent a workflow in which there are compatible surgical sponges, as previously described, but also other fluid-absorbing articles. Again, these items may not have tags detectable by the data reader 44, or the tags are not predefined in the memory as being compatible. For example, these articles may be "off-the-shelf" items such as blue towels, blue chux, peri-pads, or the like. While the type of these articles may not be automatically recognizable by the surgical sponge management system 10 from the data reader 44, the memory may have dry weights stored for each of these articles. The dry weights may have been previously entered into a database.

Figure 14A:
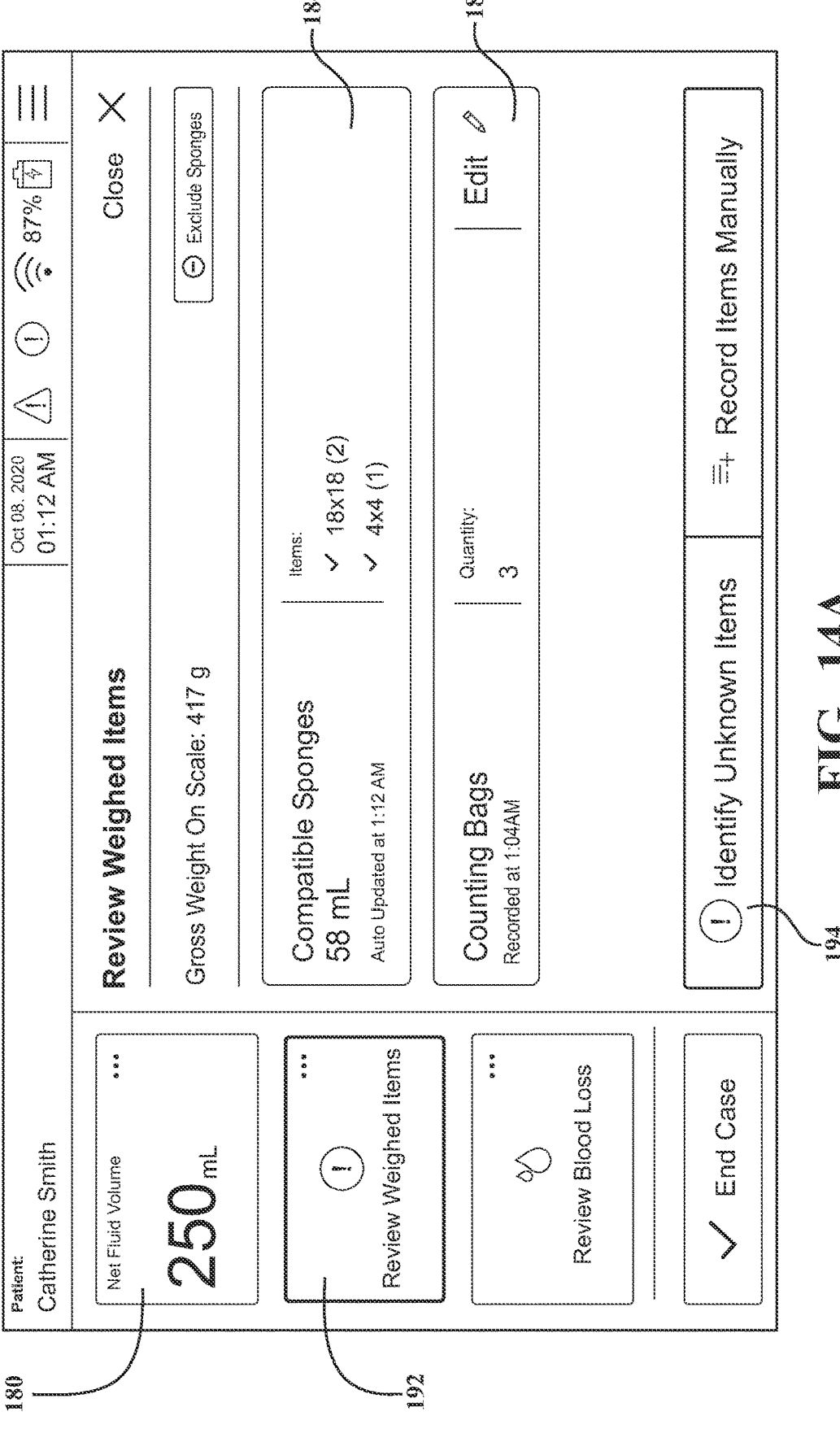
FIGS. 14A-14D are GUI screenshots of a workflow for estimating blood loss with the system in which additional fluid-absorbing articles are being used in addition to compatible surgical sponges.
Figure 14B:
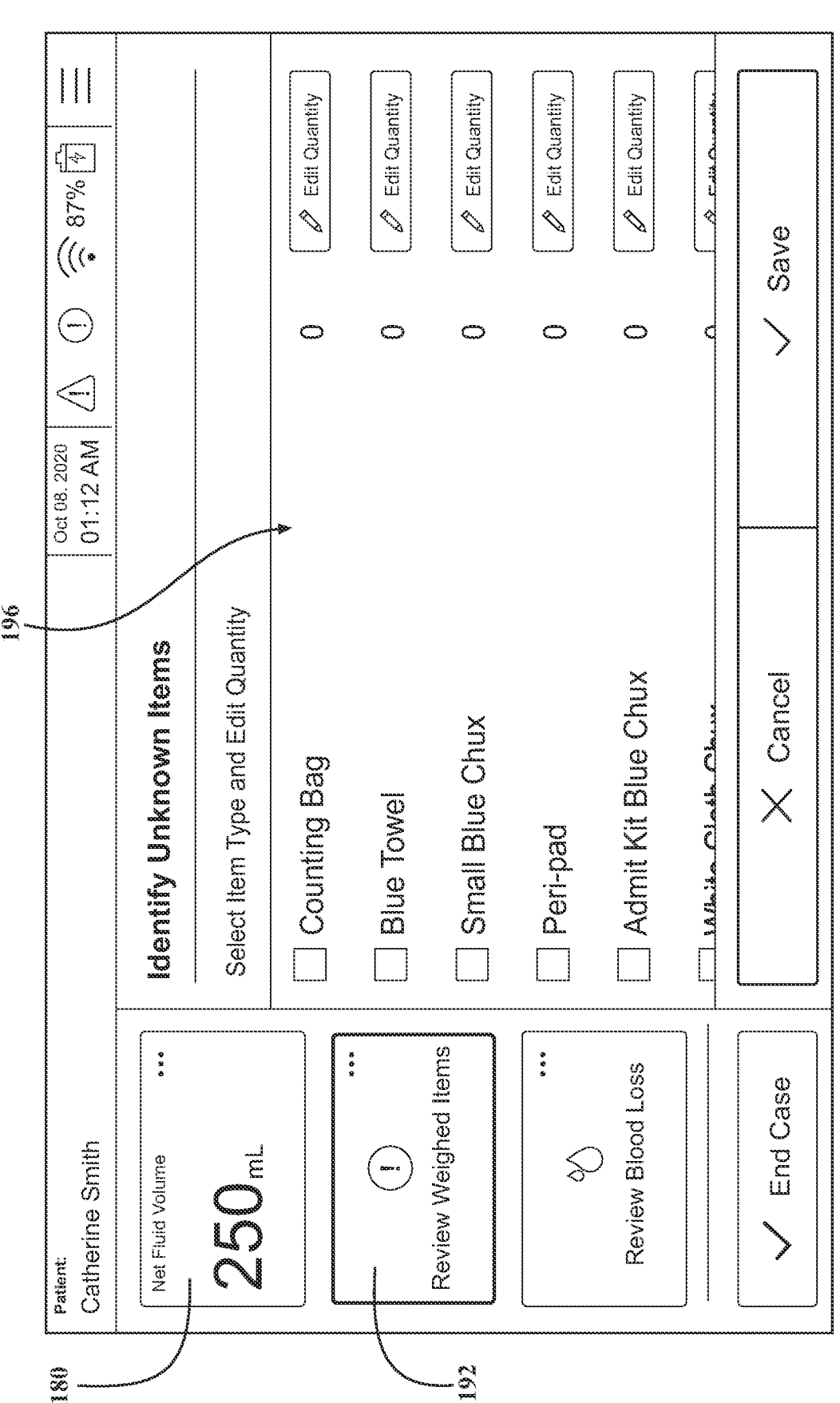
Figure 14C:
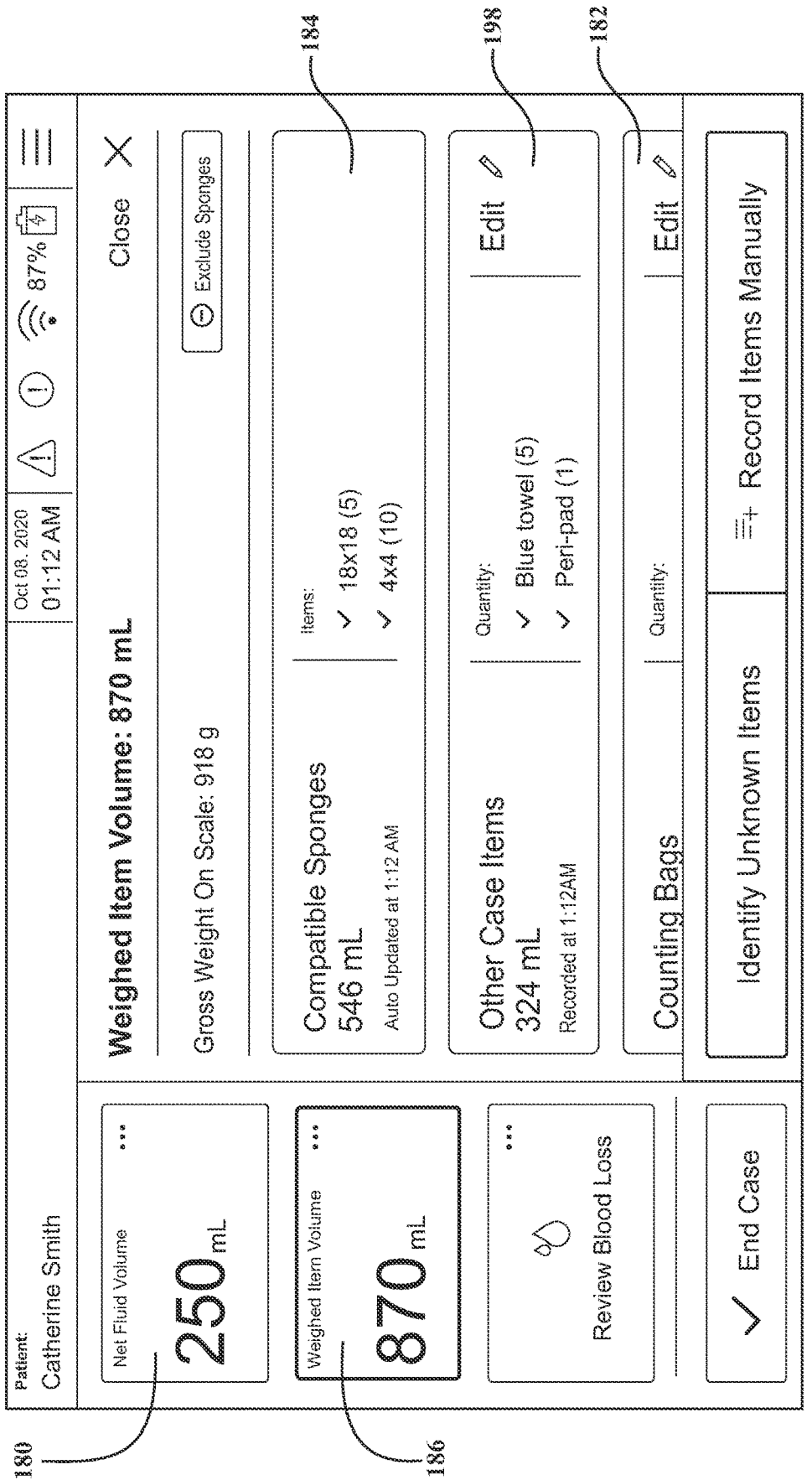
Figure 14D:
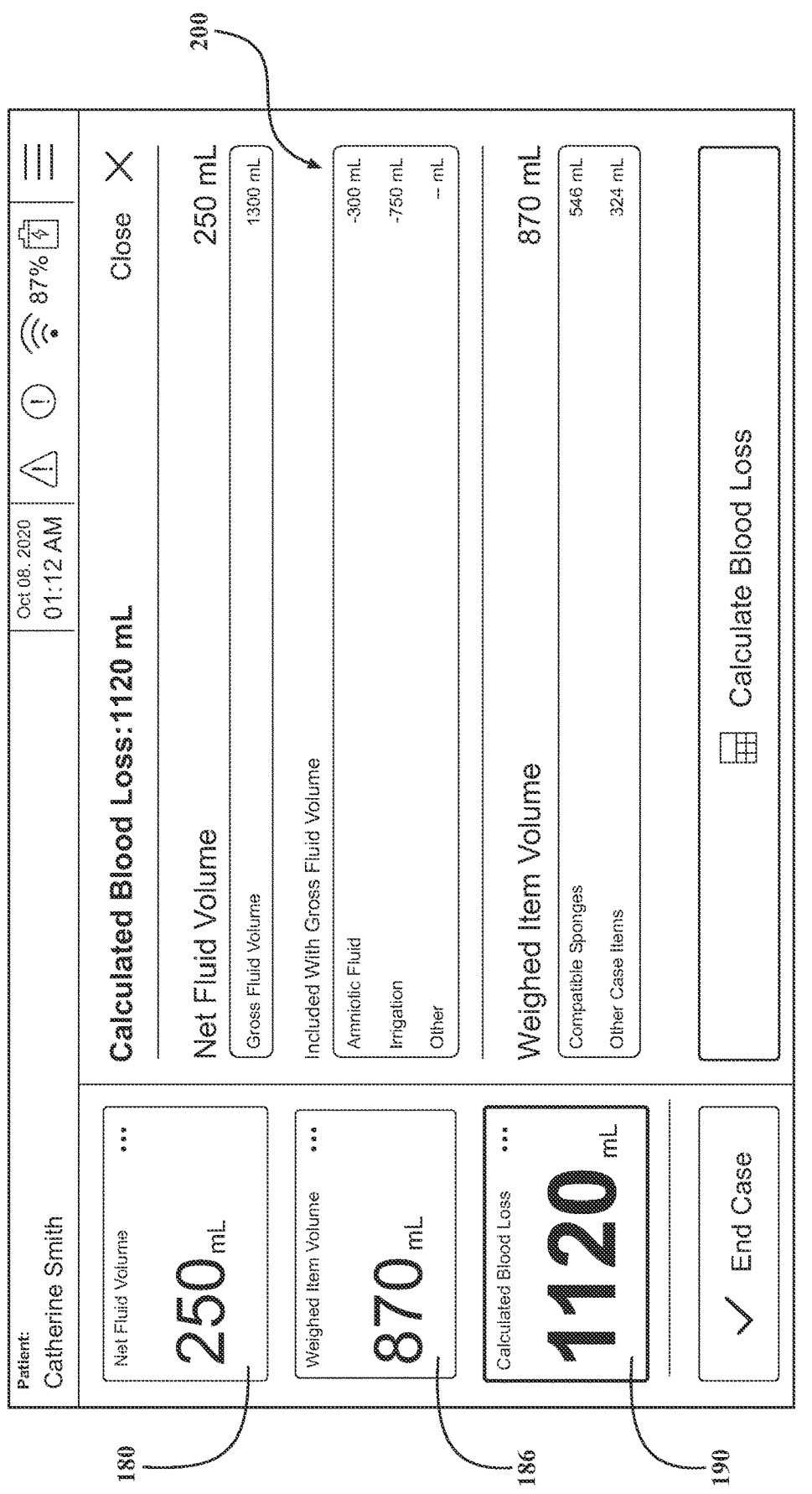

In the workflow, the user may deposit the fluid-absorbing article into the counting bag. Since the fluid-absorbing article may not include a tag detectable by the data reader 44, the processor determines that the change in the measured weight is not correlated to the counting out of a surgical sponge, and in particular a compatible surgical sponge. Tile 186 of FIGS. 13A and 13B, which displayed the weighed item value, is altered to tile 192 generally representing an alert. Further, tile 194 may become visually emphasized or altered to be selectable by the user. The tiles 192, 194 represent to the user that an "unknown item" is being assumed by the software based on the change in the measured weight not being correlated to the counting out of a compatible surgical sponge. The user may select the tile 194, after which the article list field 196 of FIG. 14B is displayed. The user may select one or more of the fluid-absorbing articles from the article list field 196. Once saved, the GUI screenshot of FIG. 14C may be provided in which tile 198 displays the fluid-absorbing articles, in addition to tile 182 displaying the counting bags and tile 184 displaying the compatible surgical sponges. The tile 198 includes the recording date and time, and type and the quantity of the fluid-absorbing articles. In this case, the articles are three blue towels and one peri-pad. Since the user has now accounted for the change in the measured weight as detected by the weighing means, the tile 192 of an alert has returned to the tile 186 in which the weighed item volume is displayed, which in this case is a sum of the weighed item volume of the compatible surgical sponges and the weighed item volume of the other fluid-absorbing articles. Once the user has completed the process or as otherwise desired, the total estimated blood loss may be calculated and displayed in tile 190, as shown in FIG. 14D. Further, the GUI screenshot of FIG. 14D further may provide a summary field 200 with a breakdown of the type and quantity of the fluids that are represented in each of the net fluid volume displayed in tile 180, the weighed item volume displayed in tile 186, and the estimated blood loss displayed in tile 190.

Figure 15A:
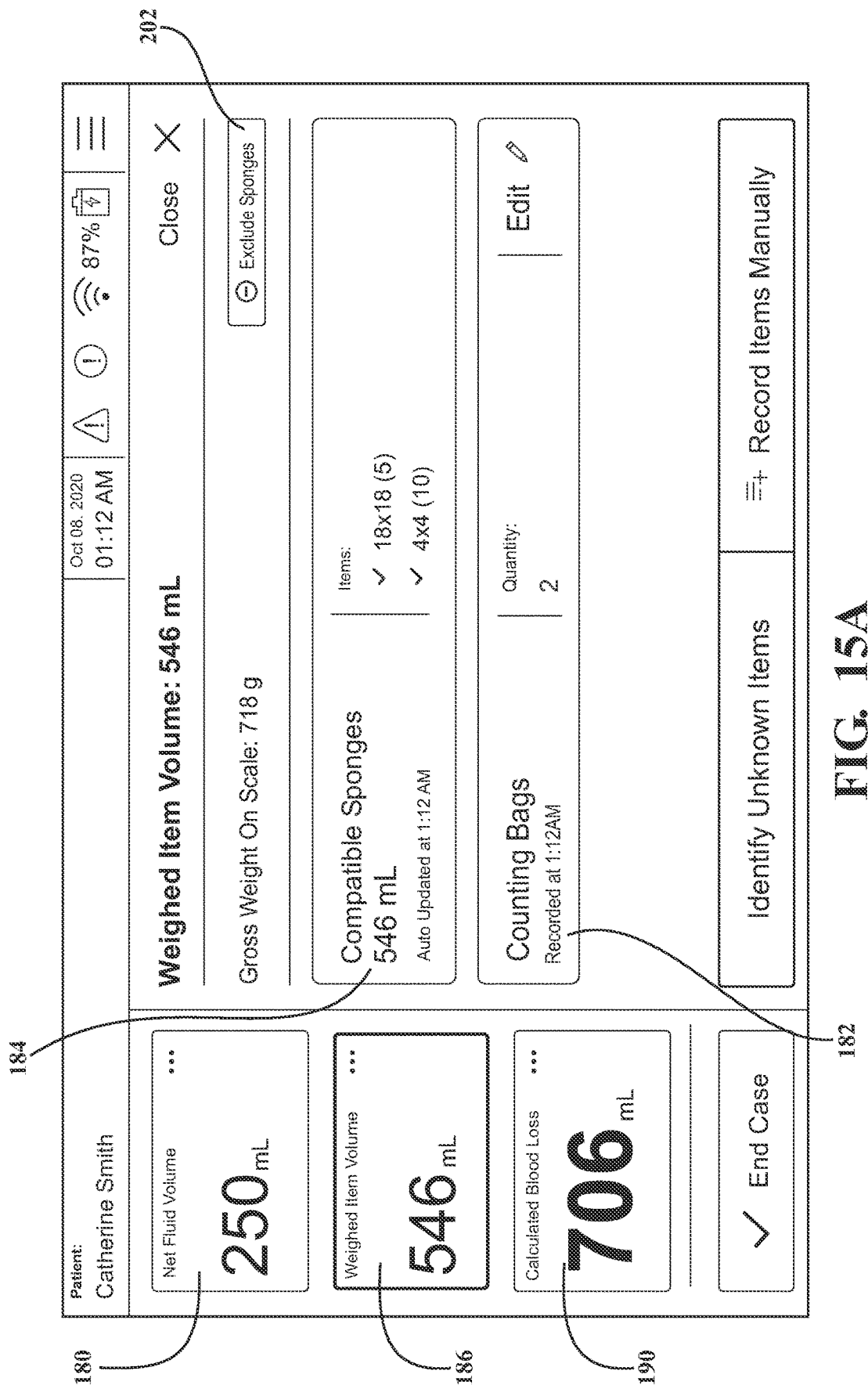
FIGS. 15A-15D are GUI screenshots of a workflow for estimating blood loss with the system in which one or more of the surgical sponges may be excluded from a weighed item volume.
Figure 15B:
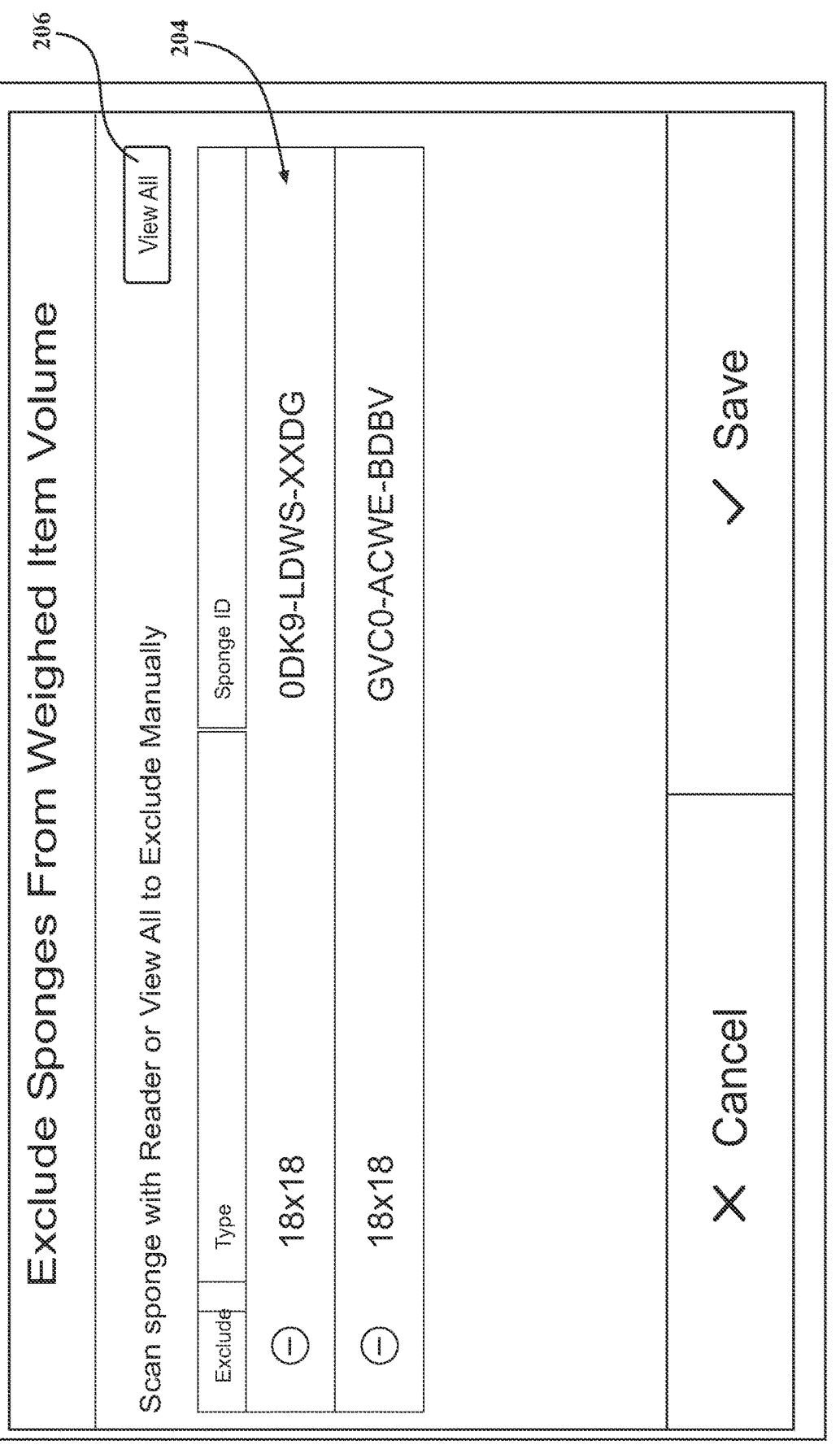
Figure 15C:
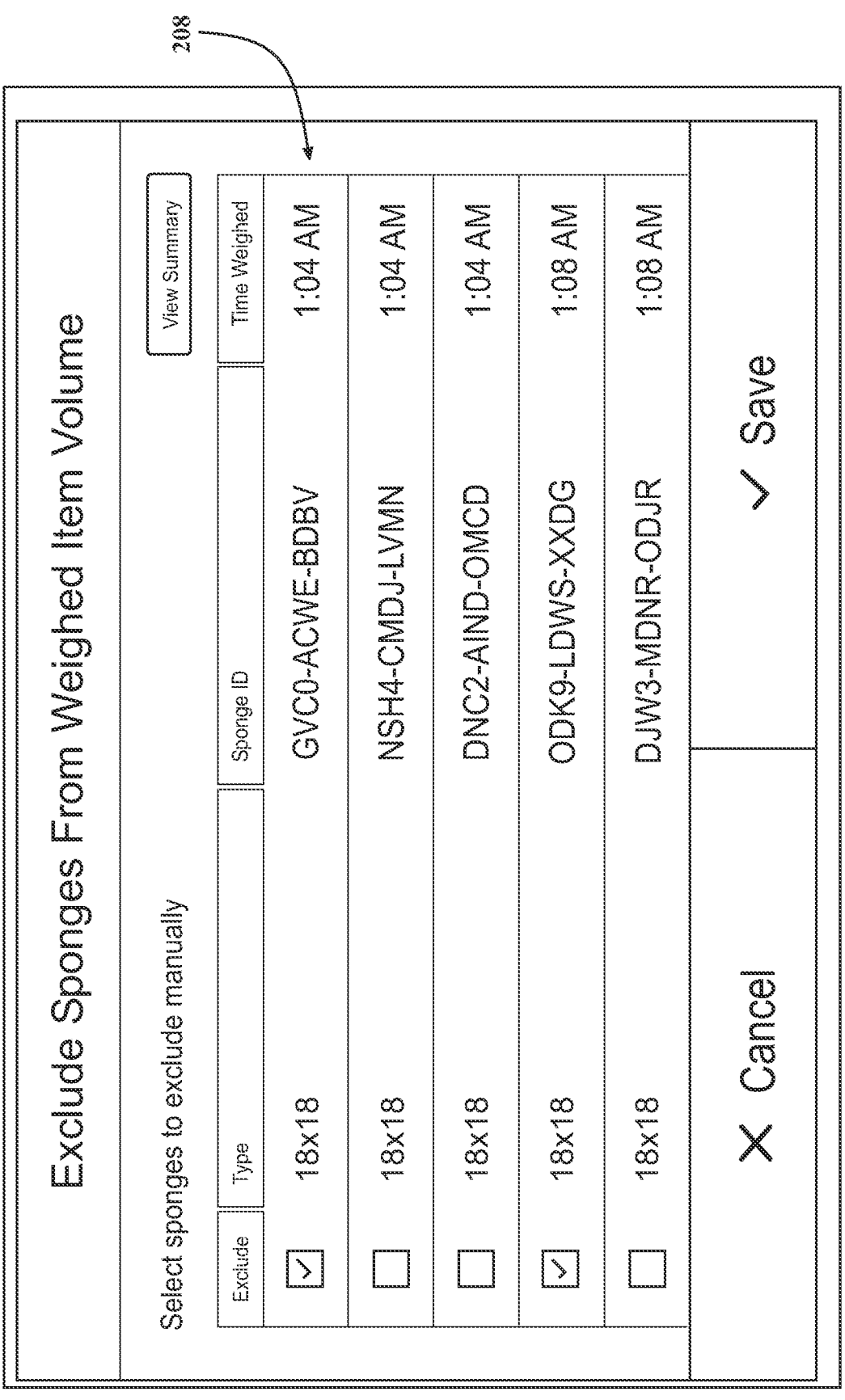
Figure 15D:
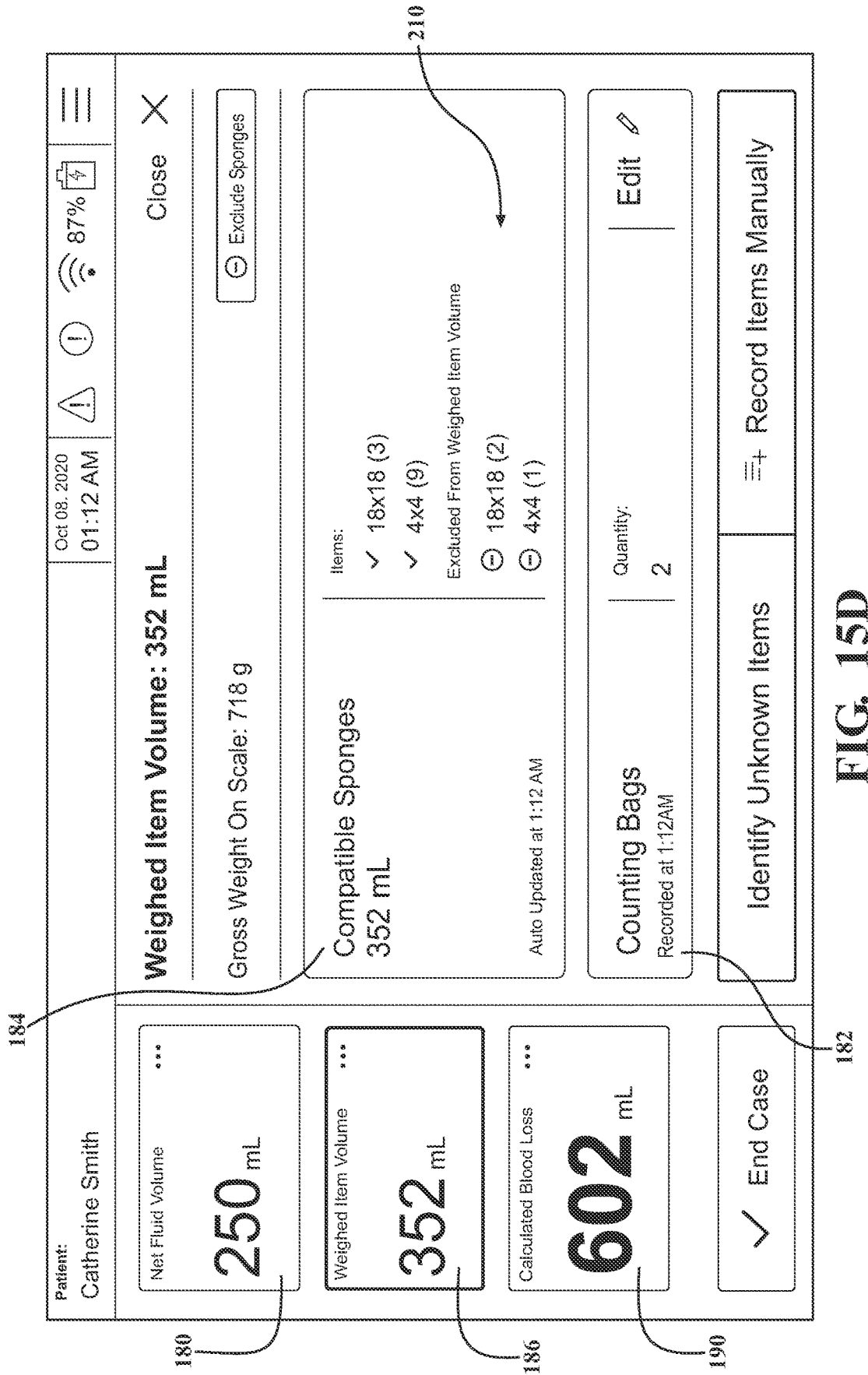

As previously mentioned, the user may be provided with the option to exclude the surgical sponges determined to have absorbed mostly or only non-blood fluids. Such a workflow is described with reference to the GUI screenshots of FIGS. 15A-15D. FIG. 15A, like FIG. 13A, includes the tiles 180, 182, 184, 186, 190 displaying the respective information including the weighed item volume associated with the compatible surgical sponges. In the present example, however, three of the compatible surgical sponges have been visually determined by the user to have absorbed excess non-blood fluid such as amniotic fluid. As such, the user wishes to exclude the weight associated with those surgical sponges from the estimated blood loss determination. However, the user may not merely remove those surgical sponges from the counting bag, as an unverified reduction in the measured weight, as sensed by the weighing means, may be designed to limit or prevent further functionality (as described herein with reference to FIGS. 16A-16C). Likewise, the user may not merely deposit the surgical sponge into the counting bag, as this would generate the "unknown item" flag previously described. Therefore, excluding the surgical sponges instructs the processor to subtract the measured weight associated with those surgical sponges, yet permit the surgical sponges to be disposed in or returned to the counting bag without issue. To that end, FIG. 15A includes virtual button or tile 202, wherein selecting the tile 202 presents the GUI screenshot of FIG. 15B (that is unpopulated initially). The exclusion of the surgical sponges may be effectuated in at least two ways. First, with the GUI screenshot of FIG. 15B displayed, the tag of the surgical sponge may be detected by the data reader 44. The excluded sponge field 204 may be populated to list the surgical sponge(s) being excluded. If the tag is undetectable or for another reason, the user may select button or tile 206 to view an active sponge field 208 on the GUI screenshot of FIG. 15C. The active sponge field 208 lists all remaining surgical sponges that are counted in. The user may visually correlate a sponge identification code presented on the tag with the corresponding sponge identification code presented in the active sponge field 208. Following completion, the GUI screenshot of FIG. 15D may be displayed in which an excluded sponge subfield 210 is displayed as part of tile 184 or its own tile. In the example, two 18×18 lap sponges and one 4×4 gauze have been listed as excluded. The tile 186 displaying the weighed item volume has been reduced accordingly as well as the tile 190 displaying the estimated blood loss.

For incompatible fluid-absorbing articles that have become saturated with a non-blood fluid, the user may elect to simply not deposit it into the counting bag, as the article may not have been counted in previously. If the fluid-absorbing article was previously counted in, an option may be provided on the GUI for it to be counted out or excluded.

Figure 16A:
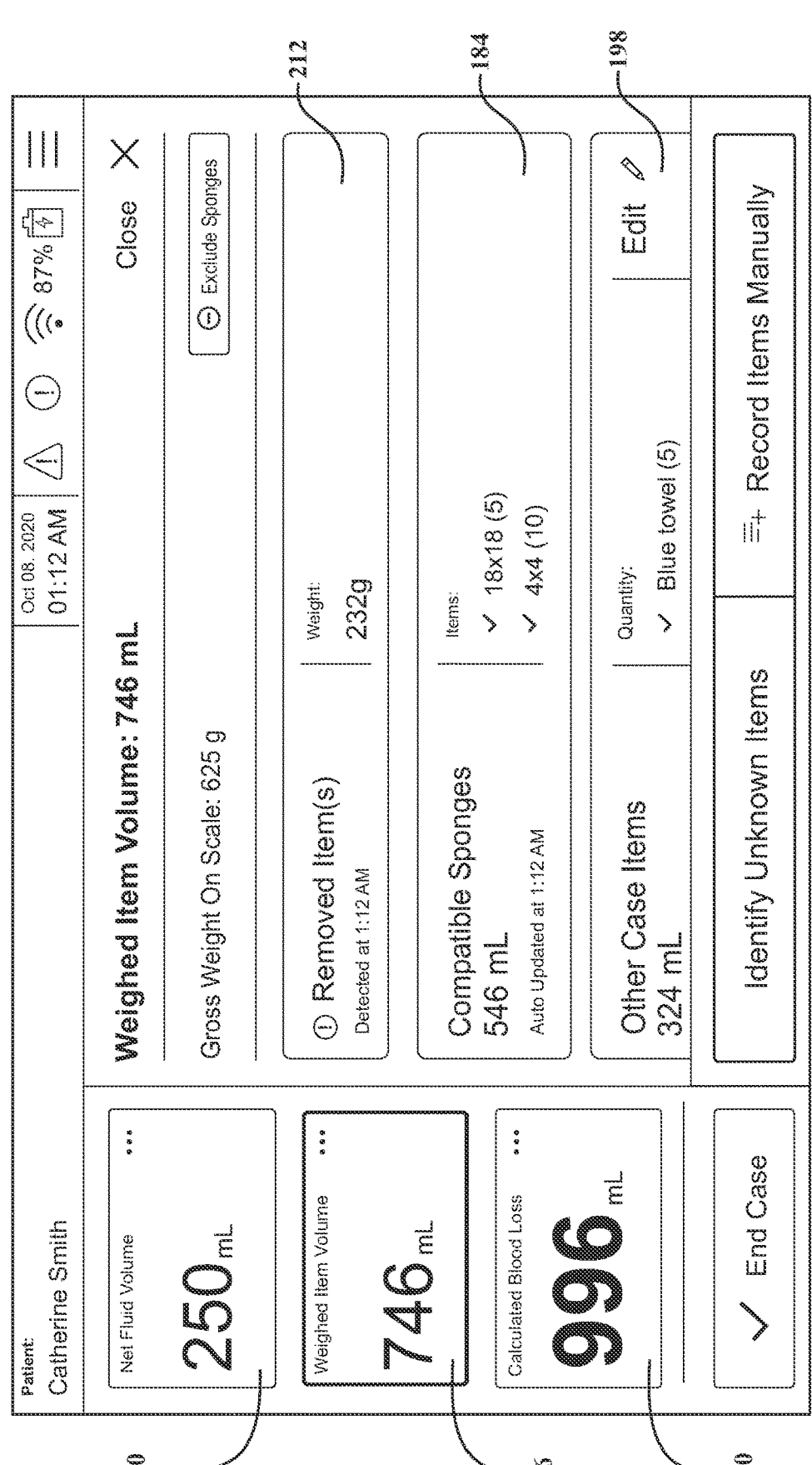
FIGS. 16A-16C are GUI screenshots of a workflow for estimating blood loss with the system in which the weighing means detects a reduction in the measured weight.
Figure 16B:
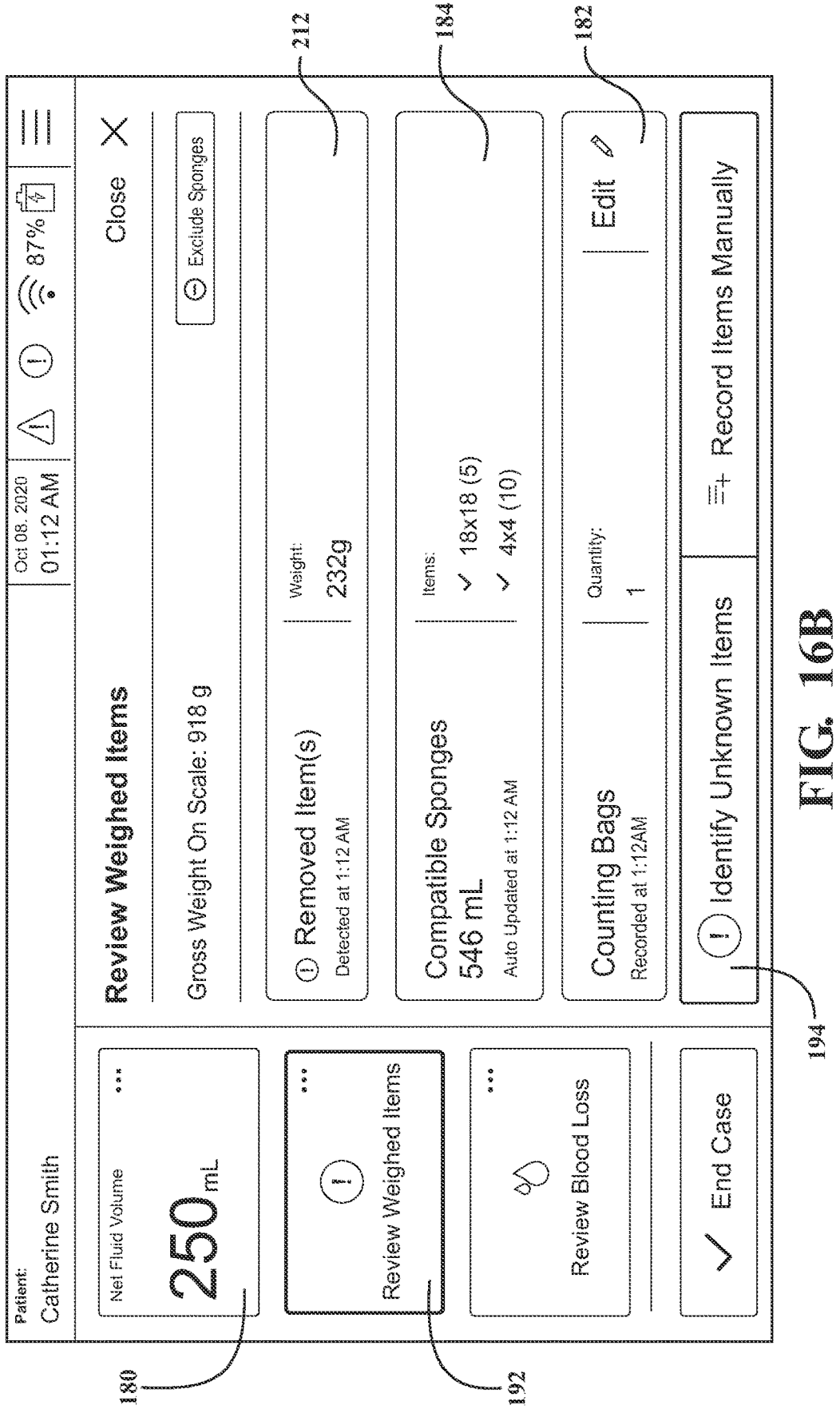
Figure 16C:
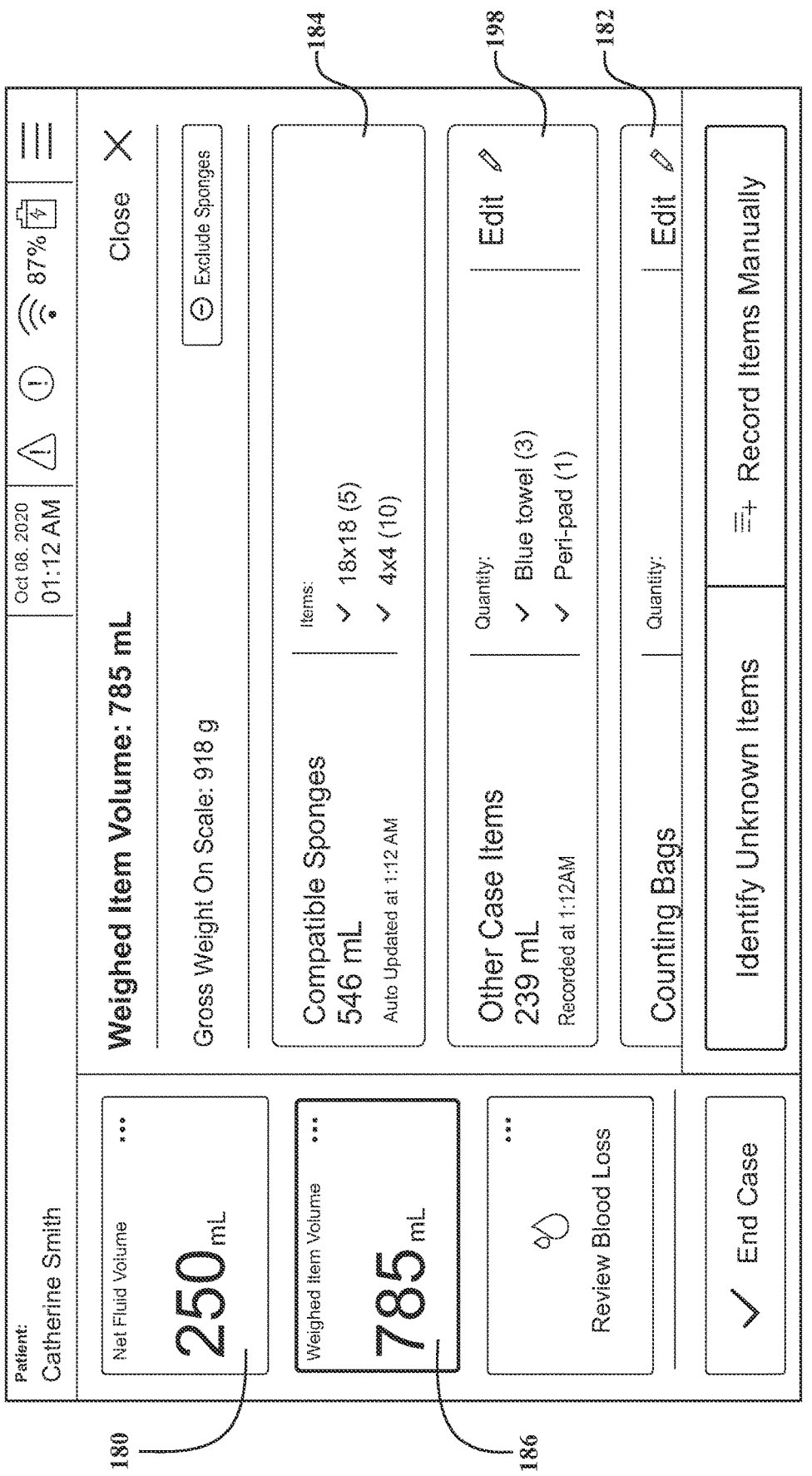

The GUI screenshots of FIGS. 16A-16C represent an instance in which the weighing means detects a decrease in the measured weight. The decrease in the measured weight may be indicative of a surgical sponge or a fluid-absorbing article being removed from the counting bag, or the counting bag being removed from or repositioned on the arm 54. FIG. 16A includes a tile 212 displaying the reduction in the measured weight as sensed by the weighing means. In one example, returning the counting bag to the arm 54 exactly as removed may merely cause the tile 212 to itself be removed. In another example, however, the user may have altered the items being returned to be supported by the arm 54, such as replacing one surgical sponge with another surgical sponge in the counting bag, or depositing additional surgical sponges to the counting bag. The GUI screenshots of FIGS. 16B and 16C illustrate such an example in which a peri-pad is added to the counting bag prior to returning the counting bag to be supported on the arm 54. Since the weight reintroduced to the arm 54 does not match the reduction in the measured weight indicated in tile 212, tile 192 is populated (and the tile 212 remains presented). Like the previous example described with reference to FIG. 14A-14D, the tile 194 may also become visually emphasized or altered to be selectable by the user. The user may select tile 194, after which the article list field 196 is displayed (see also FIG. 14B). The user may select one or more of the fluid-absorbing articles from the article list field 196. Once saved, the GUI screenshot of FIG. 16C may be provided in which tile 198 displays the fluid-absorbing articles, in addition to tile 182 displaying the counting bags and tile 184 displaying the compatible surgical sponges. Whereas tile 198 of FIG. 16A includes three blue towels, tile 198 of FIG. 16C includes the added peri-pad. Since the user has now accounted for the change in the measured weight as sensed by the weighing means, the tile 192 of an alert has returned to the tile 186 in which the weighed item volume is displayed. Once the user has completed the process or as otherwise desired, the total estimated blood loss may be calculated or recalculated, and displayed.

Certain inventive aspects of the surgical sponge management system are further disclosed with reference to the following exemplary clauses.

Clause 1—A method of estimating blood loss during a surgical procedure with a surgical sponge management system including a processor, a display in communication with the processor, a data reader in communication with the processor, memory in communication with the processor, and weighing means in communication with the processor, wherein a sponge sorter is configured to be removably coupled with the weighing means, the method comprising: sensing, with the weighing means, a change in a measured weight; determining, with the processor, whether the change in the measured weight is correlated to a compatible surgical sponge being counted out; and providing, with the display, an alert if the change in the measured weight is not correlated to the surgical sponge being counted out.

Clause 2—The method of clause 1, further comprising: receiving a user input in response to the alert; displaying on the display an article list field including fluid-absorbing articles, wherein a type of the surgical sponge has a dry weight that is stored on the memory; receiving another user input of a selection of one the fluid-absorbing articles corresponding to an item disposed in the sponge sorter; and determining, with the processor, a fluid weight of the fluid on the fluid-absorbing article based on the measured weight and the dry weight; and estimating, with the processor, blood loss associated with the fluid-absorbing article and surgical sponges based on the fluid weight; and displaying, with the display, the estimated blood loss.

Clause 3—A method of estimating blood loss during a surgical procedure with a surgical sponge management system including a processor, a display in communication with the processor and including a user interface, a data reader in communication with the processor, memory in communication with the processor, and weighing means in communication with the processor, wherein a sponge sorter is configured to be removably coupled with the weighing means and receive surgical sponges each including a tag, the method comprising: detecting, with the data reader, the tags of the surgical sponges to identify the surgical sponges as being counted in to be used during the surgical procedure, wherein each type of the surgical sponges has a dry weight that is stored on the memory; sensing, with the weighing means, a change in measured weight of the surgical sponges with the surgical sponges disposed in the sponge sorter; receiving a user input to the user interface to facilitate exclusion of one of the surgical sponges for being saturated with non-blood fluid; identifying the one surgical sponge to be excluded; determining, with the processor, a fluid weight of the fluid on the other surgical sponges based on the measured weight and the dry weights of the other surgical sponges; and estimating, with the processor, blood loss associated with the other surgical sponges based on the fluid weight; and displaying, with the display, the estimated blood loss.

Clause 4—The method of clause 3, wherein the step of identifying the one surgical sponge to be excluded further comprises detecting again, with the data reader, the tag of the one surgical sponge.

Clause 5—The method of clause 3, wherein the step of identifying the one surgical sponge to be excluded further comprises receiving another user input to the user interface to select the one surgical sponge from an active sponge field displaying a list of the surgical sponges that are counted in.

Clause 6—A method of estimating blood loss during a surgical procedure with a surgical sponge management system including a base, a main support supported by the base, a processor, a display in communication with the processor, a data reader in communication with the processor, memory in communication with the processor, and weighing means in communication with the processor, wherein a sponge sorter is configured to be removably coupled with the weighing means, the method comprising: sensing, with the weighing means, a decrease in a measured weight; providing, with the display, an alert to indicate the decrease in the measured weight.

Clause 7—The method of clause 6, further comprising sensing, with the weighing means, an increase in the measured weight, wherein the increase is equal to the decrease; and removing, from the display, the alert.

Clause 8—The method of clause 6, further sensing, with the weighing means, an increase in the measured weight, wherein the increase is greater than the decrease; providing, with the display, another alert; receiving a user input in response to the alert, wherein the user input is a selection of a fluid-absorbing article corresponding to an item disposed in the sponge sorter; and determining, with the processor, a fluid weight of the fluid on the fluid-absorbing article based on the measured weight and the dry weight; and estimating, with the processor, blood loss associated with the fluid-absorbing article and other surgical sponges based on the fluid weight; and displaying, with the display, the estimated blood loss.

Clause 9—A computer program product comprising instructions configured to be executed on a processor for performing the steps of any one of clauses 1-8.

Clause 10—A surgical sponge management system comprising a processor configured to execute instructions for performing the steps of any one of clauses 1-8.

Clause 11—A dispenser assembly for a surgical sponge management system, the dispenser assembly comprising: a lower wall adapted for being supported on a main support; an upper wall opposite the lower wall; sidewalls extending between the lower wall and the upper wall; and a front wall extending between the sidewalls and defining a front opening, wherein the lower wall, the upper wall, the sidewalls, and the front wall define a first storage location configured to removably receive a carton of the sponge sorters, wherein the upper wall comprises a first retention geometry and a second retention geometry spaced apart from the first retention geometry to at least partially define a second storage location configured to removably support a carton of the surgical draping.

Clause 12—The dispenser assembly of clause 11, comprising an arm coupled to one of the sidewalls and configured to be moved away from the one of the sidewalls from an undeployed position to a deployed position.

Clause 13—The dispenser assembly of clause 12, further comprising a flanged wall extending outwardly from the sidewalls to define a recess, wherein the arm is disposed within the recess in the undeployed position.

Clause 14—The dispenser assembly of clause 12 or 13, wherein the arm is movably supported for rotational movement, linear translation, or telescopic displacement to be moved from the undeployed position to the deployed position.

Clause 15—The dispenser assembly of any one of clauses 11-14, wherein the upper wall is configured to be pivoted relative to the lower wall.

Clause 16—The dispenser assembly of clause 15, wherein the upper wall is formed integrally with the front wall, and wherein the front wall is pivotably coupled to the lower wall with a hinge.

Clause 17—The dispenser assembly of any one of clauses 11-16, wherein the upper wall, the lower wall, and the sidewalls define a rear opening with the first storage location being accessible through the rear opening.

Clause 18—The dispenser assembly of any one of clauses 11-17, wherein the lower wall slopes downwardly towards the front wall.

Clause 19—A dispenser assembly for a surgical sponge management system, the dispenser assembly comprising: an upper shell defining a front opening; and a lower shell configured to be mounted to a main support of a stand, wherein the upper shell is coupled to the lower shell to define a rear opening opposite the front opening, and further define a first storage location between the upper and lower shells, wherein the rear opening is larger than the front opening so as to permit insertion and removal of a carton of the sponge sorters or the surgical draping through the rear opening to be accessible through the front opening.

Clause 21—The dispenser assembly of clause 20, wherein the upper shell comprises a first retention geometry, and a second retention geometry spaced apart from the first retention geometry to define a second storage location external to the upper shell.

Clause 22—The dispenser assembly of clause 20 or 21, further comprising arms pivotably coupled to the lower shell adjacent opposing sidewalls.

Clause 23—The dispenser assembly of clause 22, wherein the opposing sidewalls of the lower shell defines recesses, wherein each of the arms is positioned within a respective one of the recesses in an undeployed position.

Clause 24—The dispenser assembly of clause 23, wherein the upper shell comprises a third retention geometry, and a fourth retention geometry spaced apart from the third retention geometry to further define the second storage location.

Clause 25—The dispenser assembly of clause 24, wherein the third retention geometry or the fourth retention geometry is a frame defining a slot.

The foregoing disclosure is not intended to be exhaustive or limit the disclosure to any particular form. The terminology which has been used is intended to be in the nature of words of description rather than of limitation. Many modifications and variations are possible in light of the above teachings and the invention may be practiced otherwise than as specifically described. It should be appreciated that structure and function described with reference to one of the arms is incorporated by reference to be practiced with the other one of the arms.

The invention claimed is:

1. A system for managing surgical sponges, the system comprising:
    a base;
    a main support extending from the base; and
    a dispenser assembly supported on the main support, the dispenser assembly comprising a housing defining a first storage location that is internal to the housing with the first storage location configured to removably receive a carton of sponge sorters, and a second storage location that is external to the housing with the second storage location configured to removably support a carton of surgical draping,
    wherein the housing of the dispenser assembly comprises an upper wall defining the second storage location.

2. The system of claim 1, further comprising an arm pivotably coupled to the housing and pivotable with respect to the housing between an undeployed position in which the arm is disposed within a recess of the housing, and a deployed position in which the arm extends beyond sidewalls of the housing.

3. The system of claim 2, further comprising a mounting bracket pivotably coupling the arm with the housing, wherein the arm is cantilevered.

4. The system of claim 3, wherein the arm comprises a load cell configured to sense a change in measured weight of items supported by the arm.

5. The system of claim 4, wherein the arm further comprises a beam defining a channel, and wherein the load cell is disposed in the channel and coupled to the beam.

6. The system of claim 5, wherein the arm further comprises a loading bar, and wherein the loading bar is coupled to the load cell at an end or portion opposite to the beam.

7. The system of claim 4, further comprising:
    a handle coupled to the main support;
    a module base coupled to the main support and positioned between the handle and the dispenser assembly; and
    an electronics subassembly disposed within the module base.

8. The system of claim 7, wherein the electronics subassembly comprises a processor in communication with the load cell, the system further comprising a display removably coupled to the module base and in communication with the processor, wherein the display is configured to display an estimated blood loss as determined by the processor based on the measured weight as sensed by the load cell.

9. The system of claim 1, wherein the housing comprises an upper shell, and a lower shell coupled to the upper shell, wherein the upper shell comprises a front wall defining a front opening in communication with the first storage location.

10. The system of claim 9, wherein the lower shell comprises a lower wall sloping downwardly towards the front wall.

11. The system of claim 9, wherein the housing defines a rear opening in communication with the first storage location, wherein the rear opening is larger than the front opening.

12. A system for managing surgical sponges, the system comprising:
    a base;
    a main support extending from the base;
    a dispenser assembly supported atop the main support and comprising a first storage location for removably receiving a carton of sponge sorters, and a second storage location for removably receiving a carton of surgical draping; and
    an electronics subsystem supported on the main support, the electronic subsystem comprising a module base, a display removably coupled to the module base, and a data reader removably coupled to the module base, wherein the electronics subsystem is supported on the main support between the base and the dispenser assembly,
    wherein the main support is hollow and configured to accommodate a power cable, and defines an opening in a front side of the main support to facilitate electrical connection between the power cable and the electronics subsystem, and wherein the main support defines a second opening on a rear side of the main support from which the power cable extends to be coupled to an external power source.

13. The system of claim 12, further comprising a handle supported on the main support, the handle positioned between the electronics subsystem and the base.

14. The system of claim 12, further comprising an arm coupled to the dispenser assembly and comprising a load cell configured to detect a change in measured weight of items supported by the arm.

15. A system for managing surgical sponges, the system comprising:

a base;

a main support extending from the base; and a dispenser assembly supported atop the main support and comprising a first storage location for removably receiving a carton of sponge sorters, and a second storage location for removably receiving a carton of surgical draping; and an arm pivotably coupled to the dispenser assembly between an undeployed position in which the arm is disposed within a recess of the dispenser assembly, and a deployed position in which the arm extends beyond sidewalls of the dispenser assembly.

16. The system of claim 15, further comprising a mounting bracket pivotably coupling the arm with the dispenser assembly, wherein the arm is cantilevered.

17. The system of claim 15, further comprising an arm coupled to the dispenser assembly and comprising a load cell configured to detect a change in measured weight of items supported by the arm.

* * * * *